(12) United States Patent
Kamar et al.

(10) Patent No.: US 8,547,096 B2
(45) Date of Patent: Oct. 1, 2013

(54) SIMULTANEOUS DETERMINATION OF BITUMEN AND WATER CONTENT IN OIL SAND AND OIL SAND EXTRACTION PROCESS SAMPLES USING LOW-FIELD TIME-DOMAIN NMR

(75) Inventors: Hesham Kamar, Edmonton (CA); Supriyo Ghosh, The Woodlands, TX (US); Richard Edmund Paproski, Edmonton (CA); Peter Krygsman, Guelph (CA); Barjinder Bhalla, Fort McMurray (CA)

(73) Assignees: Syncrude Canada Ltd., Fort McMurray (CA), in trust for the owners of the Syncrude Project as such owners exist now and in the future; Bruker Corporation, The Woodlands, TX (US); Bruker Ltd., Milton (CA)

( * ) Notice: Subject to any disclaimer, the term of this patent is extended or adjusted under 35 U.S.C. 154(b) by 312 days.

(21) Appl. No.: 12/823,022

(22) Filed: Jun. 24, 2010

(65) Prior Publication Data
US 2011/0316534 A1 Dec. 29, 2011

(51) Int. Cl.
*G01V 3/00* (2006.01)
(52) U.S. Cl.
USPC .......................................... 324/307
(58) Field of Classification Search
USPC ................................... 324/300–322
See application file for complete search history.

(56) References Cited

U.S. PATENT DOCUMENTS 6,185,444 B1 * 2/2001 Ackerman et al. ............ 600/410
6,630,357 B2 10/2003 Mirotchnik et al.
7,372,264 B2 * 5/2008 Akkurt et al. ................. 324/303
7,397,241 B2 7/2008 Gauthausen et al.
7,576,538 B2 * 8/2009 Meersmann et al. ......... 324/309

FOREIGN PATENT DOCUMENTS

| CA | 2325348 | 5/2002 |
| CA | 2342007 | 9/2002 |

OTHER PUBLICATIONS

Kantzas, A. Advances in Magnetic Resonance Relaxometry for Heavy Oil and Bitumen Characterization. 2009. Journal of Canadian Petroleum Technology. vol. 48(3), pp. 15-23.
Bryan, J. et al. Oil- and Water-Content Measurements in Bitumen Ore and Froth Samples using Low-Field NMR. 2006. SPE Reservoir Evaluation & Engineering. vol. 9(6), pp. 654-663.
Motta Cabrera, S.C. et al. Estimation of Bitumen and Solids Content in Fine Tailings Using Low-Field NMR Technique. 2010. Journal of Canadian Petroleum Technology. vol. 49(7), pp. 8-19.

* cited by examiner

*Primary Examiner* — Dixomara Vargas
(74) *Attorney, Agent, or Firm* — Bennett Jones LLP

(57) ABSTRACT

A method for quantifying bitumen and/or water in a sample comprising bitumen, water and solids using a time-domain nuclear magnetic resonance pulse spectrometer is provided comprising the steps of: initially saturating the magnetization of the sample so that essentially no magnetization remains in the +Z axis; subjecting the sample to a sequence of radio-frequency pulses optimized for the measurement of bitumen and water in the sample; allowing the recording of the transverse relaxation ($T_2$) echo trains after incremental longitudinal relaxation to produce a raw TD-NMR data set for the sample; and determining the amount of bitumen and water by means of a partial least squares optimization based chemometric model relating TD-NMR data sets obtained from a training set of samples comprising bitumen, water and solids to the training samples' corresponding reference values obtained from a standard analysis method for determining bitumen and water.

8 Claims, 21 Drawing Sheets

SIMULTANEOUS DETERMINATION OF BITUMEN AND WATER CONTENT IN OIL SAND AND OIL SAND EXTRACTION PROCESS SAMPLES USING LOW-FIELD TIME-DOMAIN NMR

FIELD OF THE INVENTION

The present invention relates to a method for determining bitumen and/or water concentration in an oil sand or oil sand process sample. More particularly, time domain nuclear magnetic resonance (TD-NMR) is used to quantify the bitumen and water content simultaneously, without a drying step, using an optimized pulse sequence that utilizes both the longitudinal relaxation ($T_1$) and the transverse relaxation ($T_2$) contrasts between the bitumen and water in the sample.

BACKGROUND OF THE INVENTION

Oil sand comprises bitumen (a heavy oil), water and solids. The bitumen present in the oil sand can be extracted in situ or mined first and then subjected to a water extraction process. It is important to be able to measure the content of bitumen, water and/or solids in oil sand samples, as well being able to quickly determine the bitumen, water and/or solids content of various process streams formed during bitumen extraction.

The Dean-Stark extraction method is currently the gold standard for determining bitumen, water and/or solids content of a sample. A weighed sample is separated into bitumen, water, and solids by refluxing toluene in a Soxhlet extraction apparatus. Condensed toluene and co-distilled water are continuously separated in a trap designed to recycle the solvent through the extraction thimble, dissolving the bitumen present in the sample, while the water is retained in the trap. Full extraction of bitumen from the solids can often take hours to complete. Once the three components have been physically separated, they can be determined by various means.

Given the long analysis time of Dean-Stark extraction, faster methods are often used to monitor a continuous extraction train used for extracting bitumen from oil sand. These fast methods typically sacrifice some accuracy and/or repeatability in order to achieve a shorter analysis time. They often rely on an extraction step, filtration step, and/or drying step to separate various components prior to measurement, which adds to the total analysis time. Extraction process conditions can quickly change within minutes, making ever shorter analysis times desirable.

It is therefore desirable to develop a faster method for measuring the content of bitumen, water and solids with relatively good accuracy (compared to Dean-Stark extraction), good precision, and within as short an analysis time as possible. U.S. Pat. No. 6,630,357 discloses a method of determining the composition of a sample including heavy oil or bitumen and water using low-field NMR. However, the NMR spectrum of the sample must be taken twice, first at a relatively low temperature and then at a relatively high temperature so that a differential spectrum is created. Heating the sample to two different temperatures increases the total analysis time. Further, because only a single type of relaxation time data is measured (i.e., $T_2$), there is less complete use of available NMR relaxation information and the process is less efficient when measuring smaller quantities of bitumen in a sample that may only contain 1-2 wt. % bitumen [see Kantzas, A., "Advances in Magnetic Resonance Relaxometry for Heavy Oil and Bitumen Characterization", Journal of Canadian Petroleum Technology, 48 (3) 2009, 15-23]. All available NMR contrast (i.e., differences in $T_1$ and $T_2$) is needed to separate signals from bitumen and water molecules under these difficult circumstances. U.S. Pat. No. 7,397,241 discloses a method of determining the content of at least one component of a sample, but the experimental conditions are optimized for measuring fat and water in biological samples, not the widely varying compositions of bitumen and water in the unique matrix of oil sand core and process stream samples.

SUMMARY OF THE INVENTION

In one aspect, the present invention comprises a combined NMR relaxation method which uses a pulse sequence to obtain a $T_1$-weighted $T_2$ measurement, preceded by a saturation step, so that both the $T_1$ and $T_2$ contrasts are capitalized simultaneously, to measure the content of bitumen and water in a variety of different samples. Using such a pulse sequence, which has been optimized for detecting bitumen and water, allows for the rapid and simultaneous quantification of bitumen and water in a variety of samples, for example, samples from the various stages in an oil sand extraction process.

In one embodiment, a method for quantifying bitumen and/or water in a sample comprising bitumen, water and solids using a time-domain nuclear magnetic resonance pulse spectrometer is provided, comprising the steps of:

initially saturating the magnetization of the sample so that essentially no magnetization remains in the +Z axis;

subjecting the sample to a sequence of radio-frequency pulses optimized for the measurement of bitumen and water in the sample;

allowing the recording of the transverse relaxation ($T_2$) echo trains after incremental longitudinal relaxation to produce a raw TD-NMR data set for the sample; and determining the amount of bitumen and water by means of a partial least square optimization based chemometric model relating raw TD-NMR data sets obtained from a training set of samples comprising bitumen, water and solids to the training samples' corresponding reference values obtained from a standard analysis method for determining bitumen and water.

In one embodiment, the $T_1$ and $T_2$ relaxation information is measured by means of a time-domain nuclear magnetic resonance spectrometer.

In one embodiment, the magnetization of the sample is saturated by applying 10 rapid 90° radio-frequency (RF) pulses to the sample.

In one embodiment, the optimized sequence of radio-frequency pulses for measuring extraction process stream samples is such that there are 50 transverse relaxation echoes acquired at 27 $T_1$ points, exponentially spread from 20 ms through 3000 ms, and the last stretch of $T_2$ measurement comprises 1000 echoes spaced 0.25 ms apart (hereinafter referred to as "Pulse Sequence A"). Four replicate scans of this pulse sequence produce adequate signal to noise ratios to measure extraction process stream samples with acceptable accuracy and precision, yielding an NMR analysis time of about 90 seconds.

In one embodiment, the optimized sequence of radio-frequency pulses for oil sand samples is such that there are 50 transverse relaxation echoes acquired at 27 $T_1$ points, exponentially spread from 1 ms through 200 ms, and the last stretch of $T_2$ measurement comprises 1000 echoes spaced 0.15 ms apart (hereinafter referred to as "Pulse Sequence B"). Thirty two replicate scans of this pulse sequence produce adequate signal to noise ratios to measure oil sand samples with acceptable accuracy and precision, yielding an NMR analysis time of about 90 seconds.

In one embodiment, the standard analysis method is Dean-Stark extraction for measuring water and bitumen in a reference sample.

In one embodiment, the chemometric model is a computer program for partial least squares modeling,

DETAILED DESCRIPTION OF PREFERRED EMBODIMENTS

Figure 1:
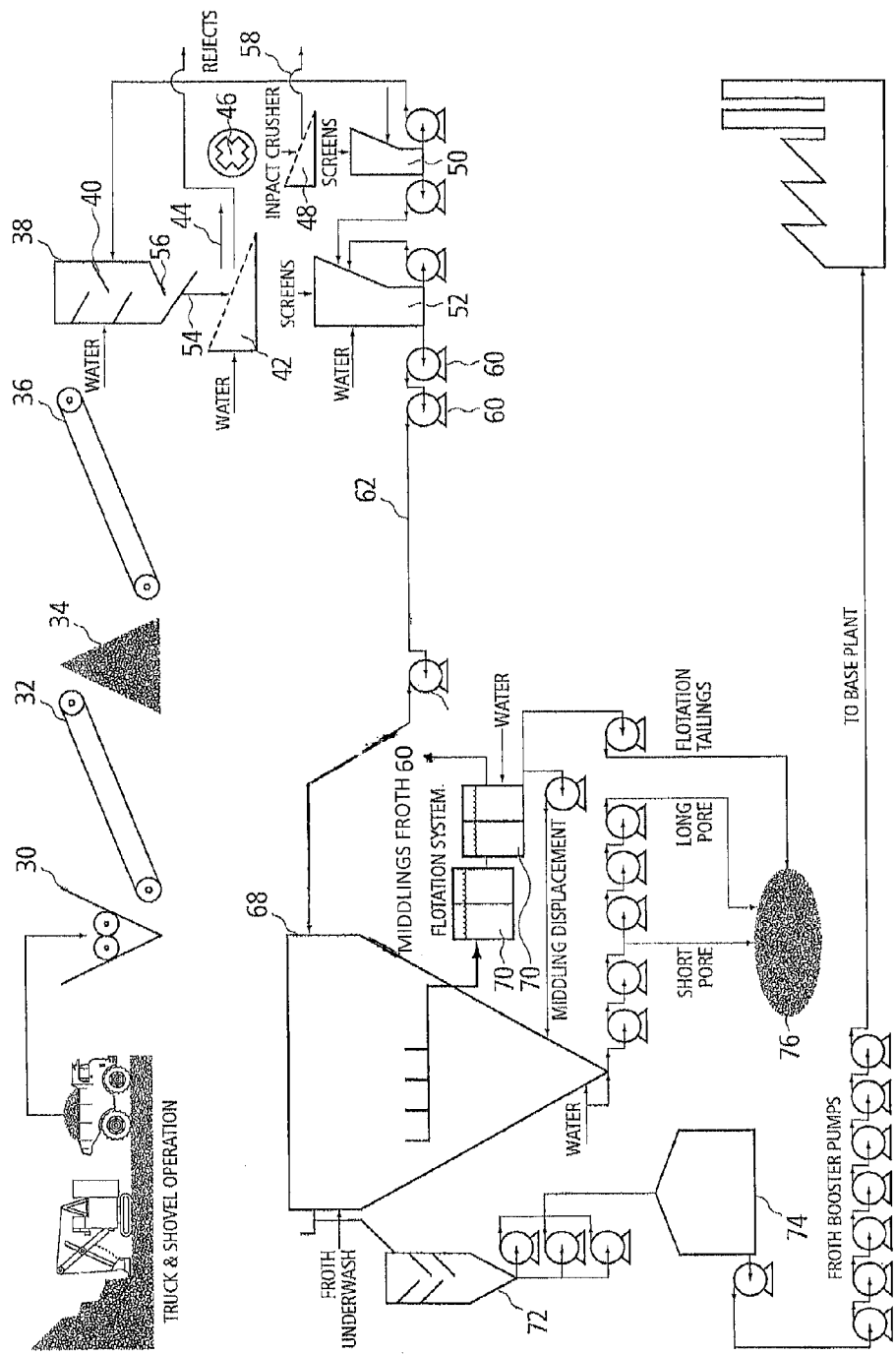
FIG. 1 is a schematic of an industrial scale oil sands mining and extraction process.

The NMR instruments used in the following examples are low field, NMR spectrometers, which record signals from hydrogen containing molecules present in an oil sand or oil sand process sample. When working within the limitations of the detection scheme of the system, the challenge is to choose the best pulse sequence and experimental parameters to record data that reflects all hydrogen-containing environments within the sample that are relevant to the components of interest. The time-domain signals, obtained through a well-designed low-field NMR experiment, reflect the number of relevant hydrogen atomic nuclei present in the entire sample as well as their characteristic relaxation (transverse and longitudinal) and diffusion behaviors.

In the case of low field time domain NMR, it was found that only measuring an oil sand sample's longitudinal relaxation time $T_1$ or the transverse relaxation time $T_2$ alone was not sufficient to accurately determine the content of the bitumen and water in the sample, simultaneously. However, it was found that a combination of the information derived from $T_1$ and $T_2$ relaxation times significantly improved the measurement statistics. Thus, NMR measurements using specific NMR pulse sequences were obtained for fast and reliable quantitative determination of bitumen and water in oil sand and oil sand extraction process samples. Because bitumen and water differ in both their longitudinal and transverse relaxation properties, using a 'combined relaxation' method with a specifically designed NMR pulse sequence allows for the simultaneous capitalization of the $T_1$ and $T_2$ contrasts of each.

In accordance with the present invention, an oil sand extraction process sample or as-mined oil sand sample is first placed in a static magnetic field which aligns the nuclear spin systems in the sample so that a net magnetization vector is produced aligned with the external magnetic field direction, called the "longitudinal" or "Z-axis" direction in common NMR terminology. NMR saturation pulses are then applied to the sample to saturate the nuclear spin magnetization so that the z (longitudinal) component of the magnetization is nearly zero; this is known to those skilled in the art as "saturation of magnetism". Thus, the longitudinal component of the magnetization is essentially at zero. In one embodiment, the saturation pulses comprise ten (10) rapid 90° radio-frequency (RF) pulses that are spaced more closely together as the countdown of pulses proceeds from 1 to 10. It is understood that other series of pulses can be used to saturate the signal at the beginning of the pulse sequence.

A combined recovery and transverse relaxation sequence of NMR pulses is then applied to the sample. The combined relaxation sequence is such that the recovery process of the magnetization back to thermal equilibrium can be followed in a single scan. The pulse sequence is essentially a $T_1$-weighted $T_2$ measurement, with parameters optimized for oil sand extraction samples (e.g., bitumen froth, middlings, oil sand tailings, etc) or as-mined oil sand samples. In one embodiment, the optimized sequence of radio-frequency pulses for extraction samples is such that there are 50 transverse relaxation echoes acquired at 27 $T_1$ points, exponentially spread from 20 ms through 3000 ms, and the last stretch of $T_2$ measurement comprises 1000 echoes spaced 0.25 ms apart. The parameters of the pulse sequence are optimized based on the thorough understanding of the NMR relaxation behavior of the various components present in the samples. Given the different diffusional environments of water in extraction samples (e.g., significant amounts of free water) versus oil sand samples (e.g., significant amounts of water-associated with clay fines), different sets of pulse sequence parameters may be required to achieve satisfactory determination of bitumen and water simultaneously in extraction samples compared to as-mined oil sand samples.

The behavior of the transverse magnetization is followed during the recovery of the longitudinal magnetization in order to fully exploit the contrast due to different $T_1$ and $T_2$ relaxations times of the bitumen and water. Thus, at each recovery point $T_2$ relaxation time is measured as well. The complex time-domain data acquired through these measurements is then used to build a chemometric model for simultaneous determination of bitumen and water without the need for a time-consuming drying step to eliminate the water or the need to analyze the samples at two different temperatures. The whole pattern of recovering and dephasing magnetization is recorded. The signal includes the combined effect of $T_1$ and $T_2$ relaxation processes, and is interpreted by Partial Least Squares (PLS) based chemometric technique. One program that can be used for evaluation is QUANT II OPUS NT software by Bruker Optics, Billerica, Mass. Other chemometric software with PLS capability could also be used for model development and data analysis.

Chemometric data processing relies on the fact that each signal pattern can be described by a combination of basic patterns with varying amplitudes. Creating this set of patterns by measurement of a large number of samples, where the bitumen and water content has been determined using more conventional measuring techniques, such as Dean Stark analysis, allows one to build the calibration model which can then be used for the quantitative analysis of unknown samples. Once the model is built using a proper training dataset, this method is able to accurately determine the bitumen and water content in a variety of samples in about 90 seconds.

Thus, by optimizing the pulse sequence parameters for a specific type(s) of sample (e.g., as-mined oil sand or oil sand extraction samples such as froth, middlings and tailings), one can take advantage of $T_1$, $T_2$ and diffusion contrast simultaneously, making the resolution of signal from multiple components possible. As a result, one can obtain very good correlation between TD-NMR prediction and reference values from primary industry-recognized methods.

EXAMPLE 1

A typical commercial oil sand operation is shown in FIG. 1. More particularly, oil sand is surface mined and fed into a primary crusher 30 of the double roller type, to reduce the oversize to less than 24". The crushed oil sand is carried by conveyer to surge pile 34 of oil sand. Oil sand from surge pile 34 is fed by conveyer 36 to a mix box 38, comprising a plurality of inclined plates 40. Hot slurry water is also added to the mix box to form an oil sand slurry. Mixing can also occur in a cyclofeeder or other slurry preparation units as are known in the art. Product slurry 54 leaves the bottom outlet 56 of mix box 38 and passes through screen 42 and, optionally, more hot slurry water is added. Product slurry enters a pump box 52 and rejects 44 are fed to an impact crusher 46 and screened again through screen 48. Oversize rejects 58 are discarded but screened material enters pump box 50, where more hot slurry water is added and then oil sand slurry is pumped into pump box 52.

Oil sand slurry in pump box 52 is then pumped by a series of pumps 60 through conditioning pipeline 62 and the conditioned oil sand slurry (hydrotransport oil sand slurry) is then optionally diluted with water (PSV feed) and introduced into primary separation vessel 68 and retained under quiescent conditions, to allow the solids to settle and the bitumen froth to float to the top. A froth underwash of hot water is added directly beneath the layer of bitumen froth to aid in the separation. Bitumen froth, which is called primary froth, is removed from the top of the primary separation vessel 68 (PSV overflow) and then deaerated in froth deaerator 72. Once deaerated, primary froth is retained in froth tank 74 (deaerated bitumen froth).

Middlings from primary separation vessel 68 (PSV middlings) are removed and undergo flotation in flotation cells 70 to produce middlings flotation froth (secondary froth) and middlings flotation tails. Secondary froth is recycled back to the primary separation vessel 68. Tailings, the solids, water, etc. that collects at the bottom of the primary separation vessel 68 (PSV coarse tails) are removed and deposited into tailings pond 76 and/or further treated.

In this example, the amount of bitumen and water is determined during the various bitumen extraction steps. A total of 444 samples from a commercial oil sand mining/extraction operation were collected from a variety of sampling points during oil sand extraction and processing, which sampling points are listed in Table 1.

TABLE 1

Process stream sampling points from an oil sand mining/extraction operation

| Sample ID | Sample Description |
|---|---|
| 23A1 | Hydrotransport Oil Sand Slurry |
| 23B1 | Hydrotransport Oil Sand Slurry |
| 23C1 | Hydrotransport Oil Sand Slurry |
| 24A2 | Deaerated Bitumen Froth |
| 24A3 | PSV Middlings |
| 24A4 | Middlings Flotation Froth |
| 24A5 | PSV Overflow |
| 24A6 | Middlings Flotation Tails |
| 24A7 | PSV Coarse Tails |
| 24A8 | Bitumen Froth at Discharge |
| 24A9 | PSV Feed |
| 24B2 | Deaerated Bitumen Froth |
| 24B3 | PSV Middlings |
| 24B4 | Middlings Flotation Froth |
| 24B5 | PSV Froth Overflow |
| 24B6 | Middlings Flotation Tails |
| 24B7 | PSV Coarse Tails |
| 24B8 | Bitumen Froth |
| 24B9 | PSV Feed |

Samples were collected directly into 250 ml wide mouth Nalgene bottles (P/N: 2100-0008). Bruker LF90II low field NMR instrument, operating at 6.2 MHz $^1$H frequency, was used with a 89 mm diameter probe to accommodate these 250 ml bottles. The use of such an instrument avoids the need for sub-sampling and allows relatively large sample sizes to be used. Sample weights varied from 50 to 110 g for most samples, with the exception of froth samples, which varied from 25 to 45 g. Eliminating the need to sub-sample is important to avoid biases and poor repeatability associated with sub-sampling extraction process stream samples that are heterogeneous and contain solids that settle quickly.

Froth samples were analyzed without prior shaking. Other sample types were briefly shaken by hand to re-suspend the solids prior to analysis. As part of method development, some samples were preheated to 37° C. to match the temperature of the NMR probe, some were analyzed at room temperature (on average 23° C.), and some were analyzed at both room temperature and at 37° C. to allow for a comparison.

The optimized pulse sequence used to simultaneously measure the bitumen and water content in extraction process stream samples (i.e., Pulse Sequence A) used 50 transverse relaxation echoes acquired at 27 $T_1$ points, exponentially spread from 20 ms through 3000 ms. The final stretch of $T_2$ measurement comprised of 1000 echoes spaced 0.25 ms apart. The average of four consecutive scans was used to improve the signal-to-noise ratio, providing an NMR measurement time of about 90 seconds.

Following NMR analysis, the samples were analyzed using Dean-Stark extraction, as known in the art. A weighed sample is separated into bitumen, water, and solids by refluxing toluene in a Soxhlet extraction apparatus. Condensed toluene and co-distilled water are continuously separated in a trap designed to recycle the solvent through the extraction thimble, dissolving the bitumen present in the sample, while the water is retained in the trap. Full extraction of bitumen from the solids can often take hours to complete. Once the three components have been physically separated, they can be determined by various means. The Dean-Stark values were used as the accepted values when creating the training sets for the chemometric model.

After the raw TD-NMR data was collected for each sample, the raw data files were loaded into OPUS chemometric software obtained from Bruker Optics along with the corresponding Dean-Stark reference bitumen and water values. The OPUS software was used to build chemometric models using partial least squares cross-correlational technique to determine bitumen and water content from the raw TD-NMR signals.

After a batch of samples were analyzed, their results were then added to the model before analyzing the next set of samples. This step was followed in the initial phase, in order to increase the robustness of the models.

Three different sets of chemometric models were built using raw NMR signals collected on a variety of extraction process stream samples at room temperature, on samples at 37° C., or on samples at both temperatures. One advantage of building a model using signals collected at both sets of temperatures is that the model becomes more robust toward small shifts in sample temperature. Building a model with NMR signals collected at different temperatures helps train the model to account for potential temperature differences.

A low bitumen (i.e., <2.5% bitumen) model was also built based on 231 low bitumen samples (i.e., typically tailings samples). Thus, better accuracy for low bitumen extraction samples compared to Dean-Stark analysis was obtained by building a separate bitumen model for these samples. The low bitumen model was used to generate the validation results for samples with less than 2.5% bitumen shown in FIGS. 16 and 17 and reported in Tables 2 and 3.

Figure 2:
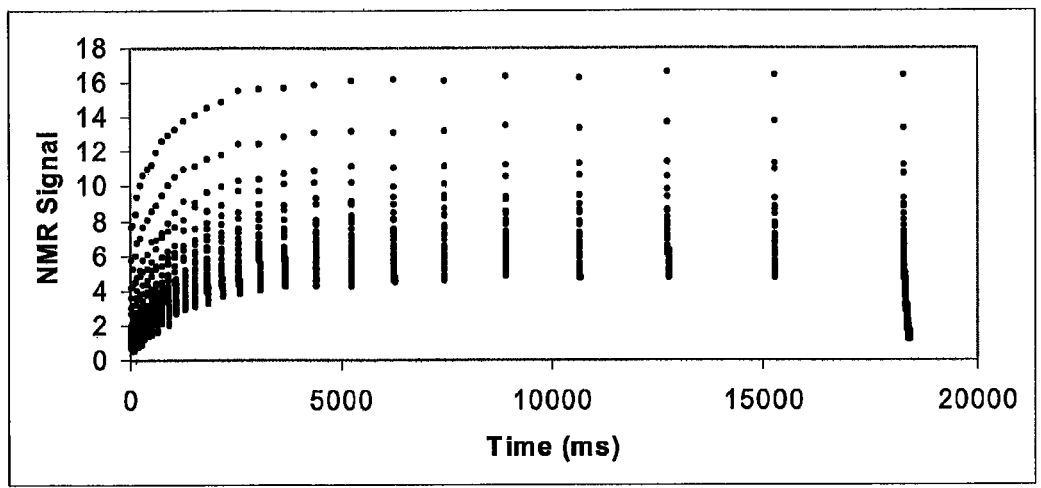
FIG. 2 shows the NMR signal versus time for a typical bitumen froth extraction sample on LF90II NMR using Pulse Sequence A (average of 4 scans, 90 seconds analysis time).
Figure 3:
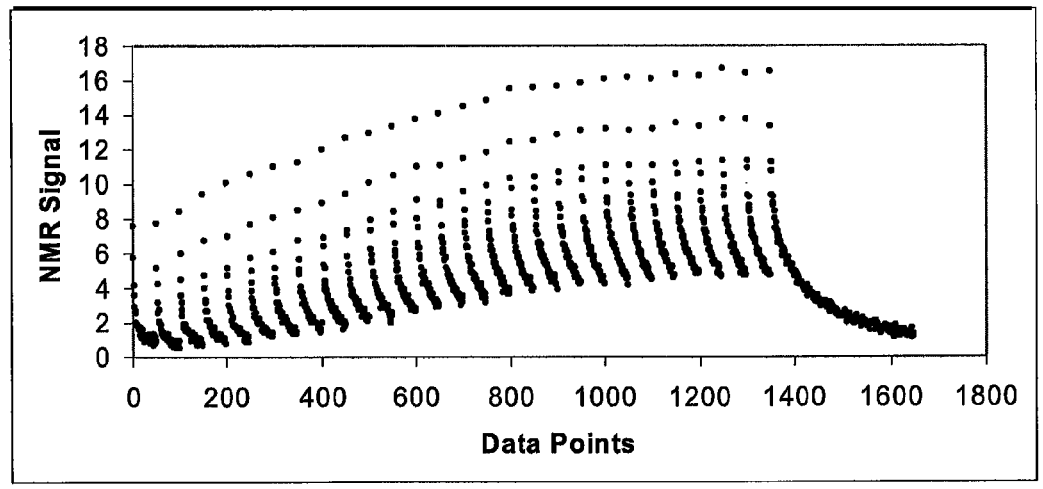
FIG. 3 shows the NMR signal versus data points for a typical bitumen froth extraction sample on LF90II NMR using Pulse Sequence A (average of 4 scans, 90 seconds analysis time).
Figure 4:
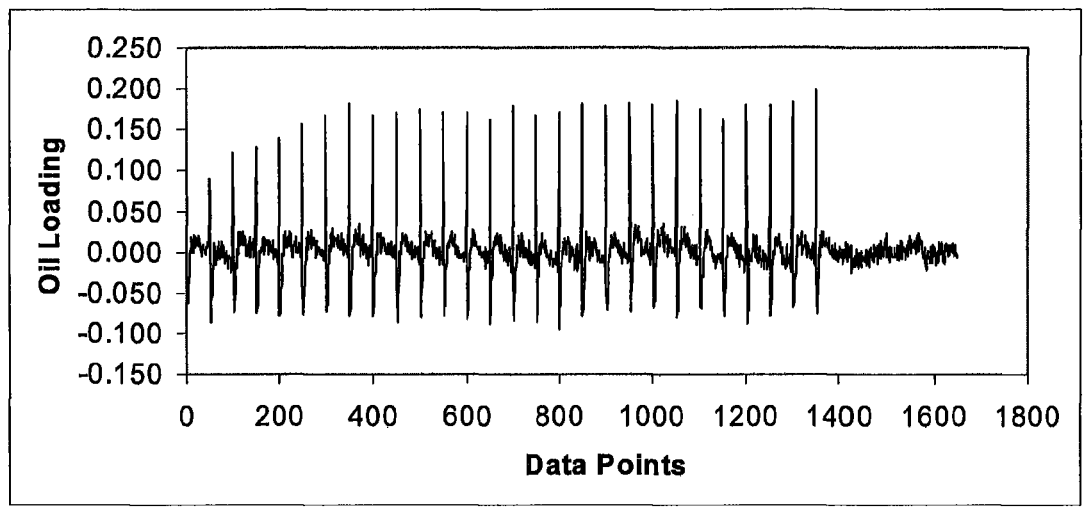
FIG. 4 shows the partial least squares bitumen model loadings for extraction samples with >2.5% bitumen on LF90II NMR using Pulse Sequence A (4 scans, 90 seconds analysis time).
Figure 5:
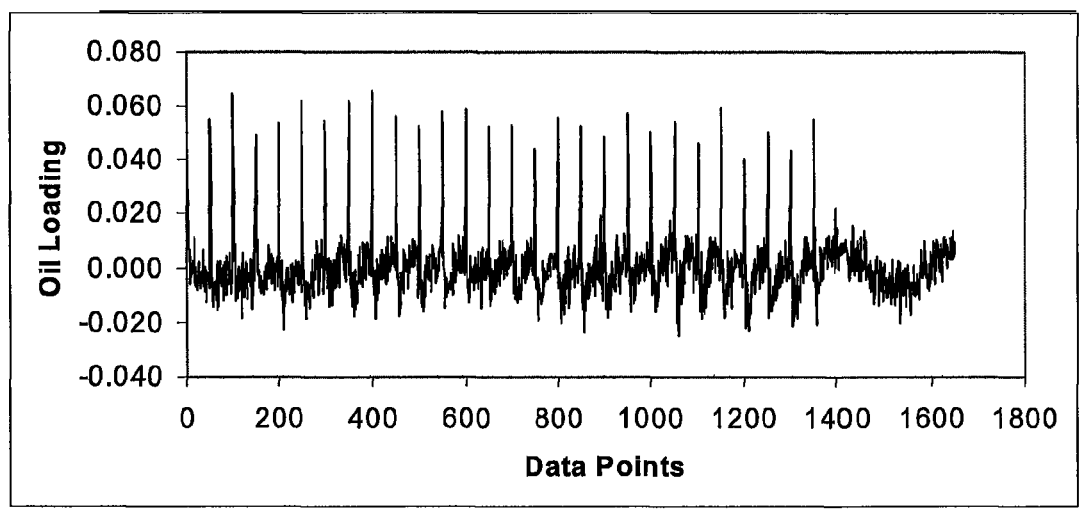
FIG. 5 shows the partial least squares bitumen model loadings for low bitumen extraction samples with <2.5% bitumen on LF90II NMR using Pulse Sequence A (4 scans, 90 seconds analysis time).
Figure 6:
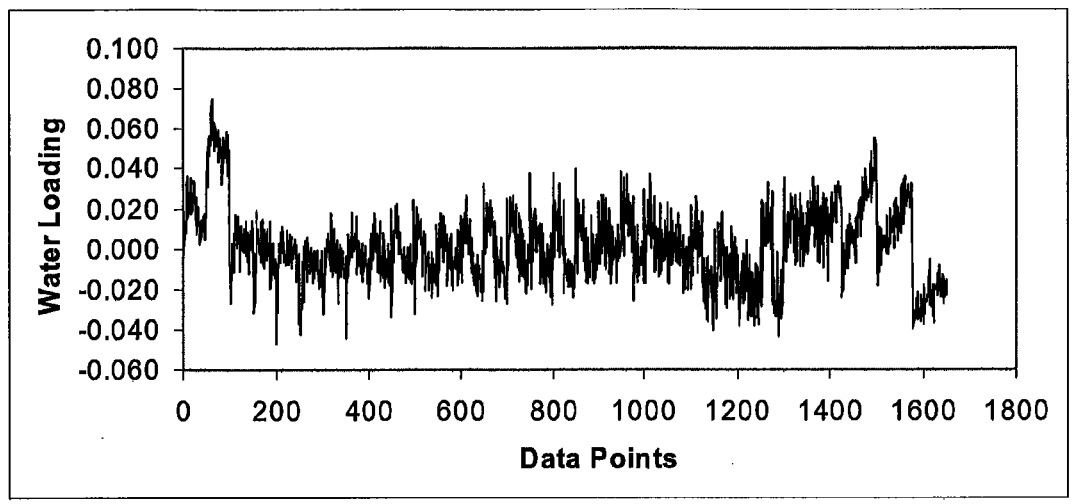
FIG. 6 shows the partial least squares water model loadings for extraction samples on LF90II NMR using Pulse Sequence A (average of 4 scans, 90 seconds analysis time).

FIG. 2 shows the raw data (NMR signal versus time) for a typical bitumen froth extraction sample on LF90II NMR using Pulse Sequence A (average of 4 scans, 90 seconds analysis time). FIG. 3 shows the raw data (NMR signal versus data points) for a typical bitumen froth extraction sample on LF90II NMR using Pulse Sequence A (average of 4 scans, 90 seconds analysis time). FIG. 4 shows the partial least squares bitumen model loadings for extraction samples with >2.5% bitumen on LF90II NMR using Pulse Sequence A (average of 4 scans, 90 seconds analysis time) and FIG. 5 shows the partial least squares bitumen model loadings for extraction samples with <2.5% bitumen on LF90II NMR using Pulse Sequence A (average of 4 scans, 90 seconds analysis time). FIG. 6 shows the partial least squares water model loadings for extraction samples with <2.5% bitumen on LF90II NMR using Pulse Sequence A (average of 4 scans, 90 seconds analysis time).

Figure 7:
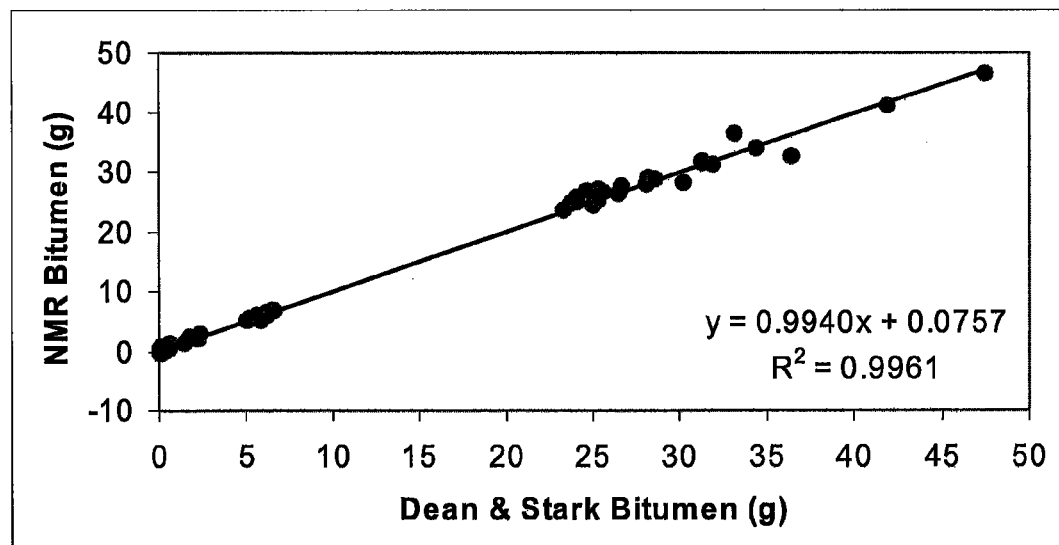
FIG. 7 shows a bitumen chemometric model at room temperature for extraction samples using Pulse Sequence A with the LF90II NMR.
Figure 8:
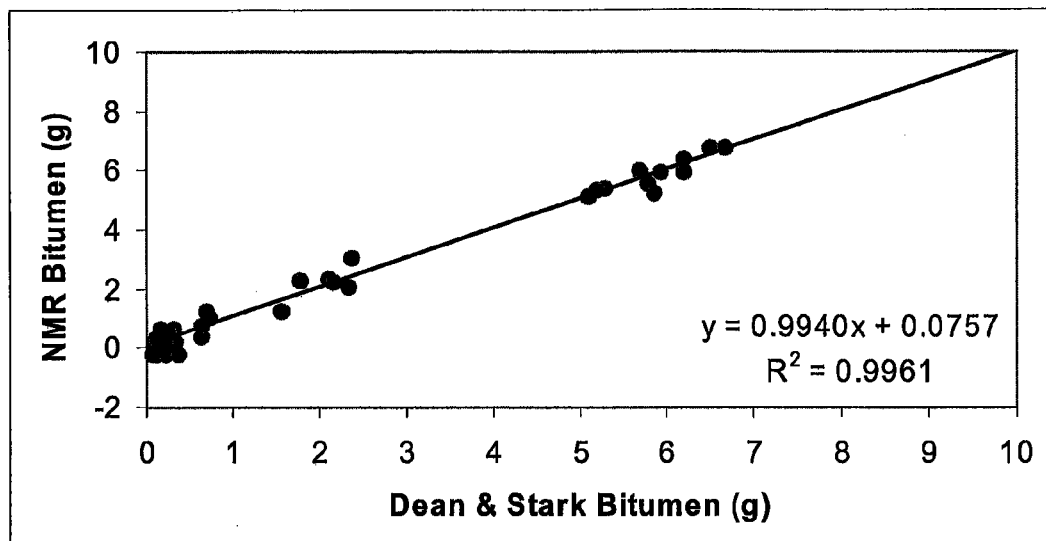
FIG. 8 shows a bitumen chemometric model at room temperature (zoomed in on the low bitumen content samples) for extraction samples using Pulse Sequence A with the LF90II NMR.
Figure 9:
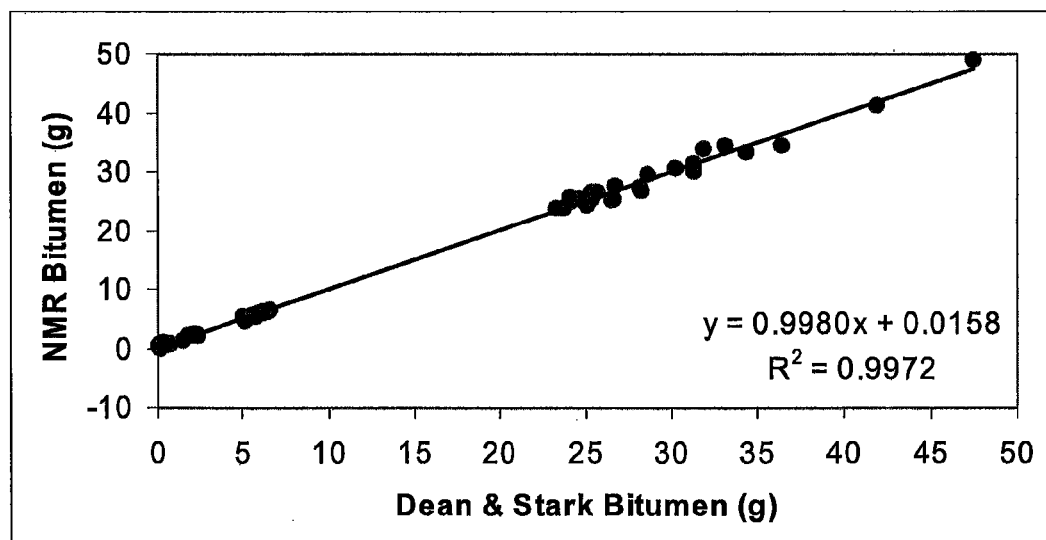
FIG. 9 shows a bitumen chemometric model at 37° C. for extraction samples using Pulse Sequence A with the LF90II NMR.
Figure 10:
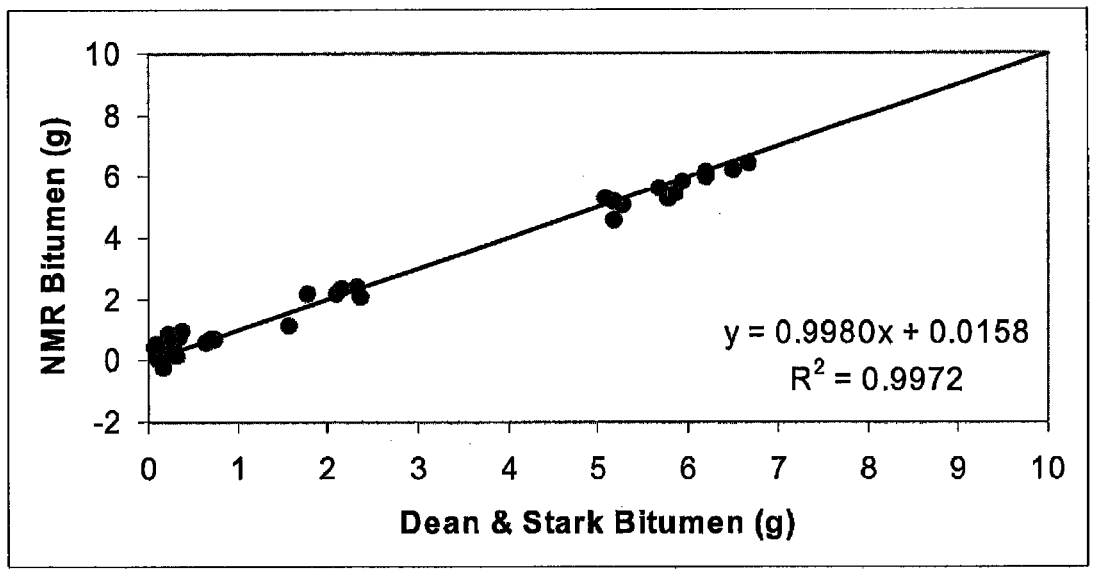
FIG. 10 shows a bitumen chemometric model at 37° C. (zoomed in on the low bitumen content samples) for extraction samples using Pulse Sequence A with the LF90II NMR.
Figure 11:
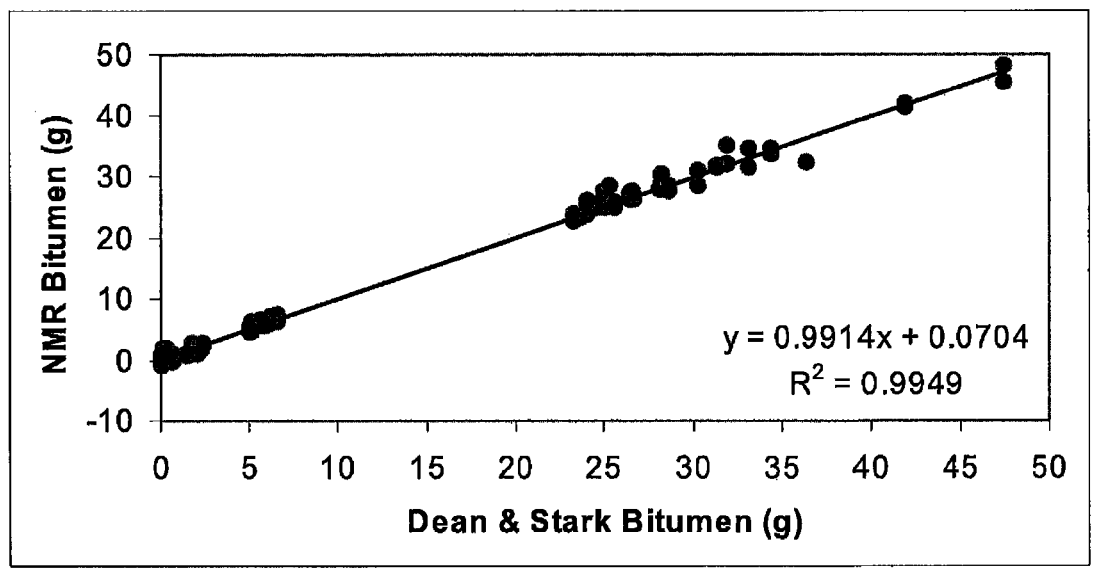
FIG. 11 shows a combined bitumen chemometric model using data collected at room temperature and 37° C. for extraction samples using Pulse Sequence A with the LF90II NMR.
Figure 12:
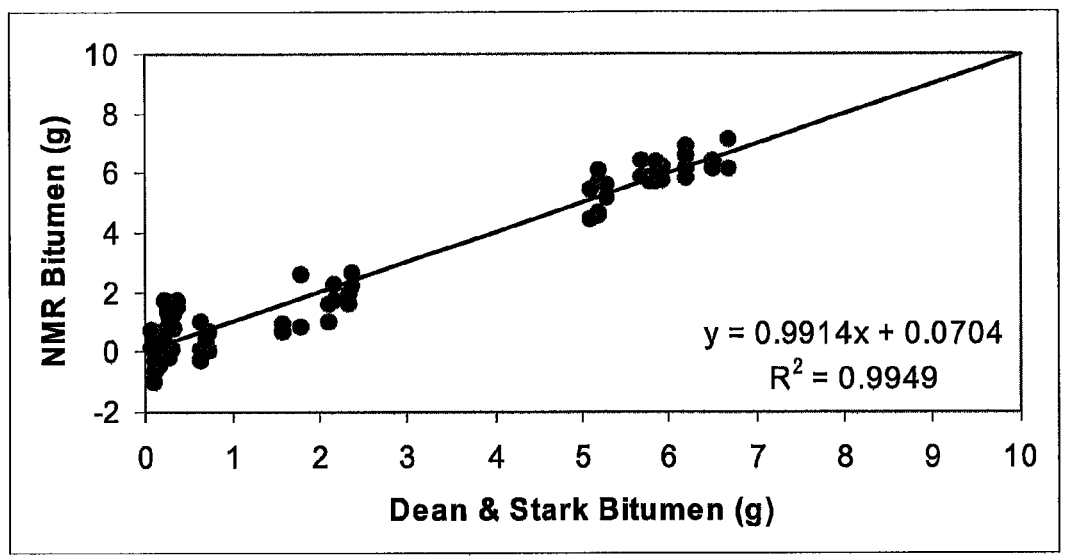
FIG. 12 shows a combined bitumen chemometric model using data collected at room temperature and 37° C. (zoomed in on low bitumen content samples) for extraction samples using Pulse Sequence A with the LF90II NMR.

FIGS. 7 and 8 show the model for bitumen using an illustrative set of 64 extraction samples at room temperature. FIGS. 9 and 10 show the model for bitumen using the same 64 samples at 37° C. FIGS. 11 and 12 show the model for bitumen using the same 64 samples at both room temperature and 37° C. The model for bitumen using the 37° C. data shows the best correlation out of the three models (R-squared closest to 1, slope closest to 1, and y-intercept closest to zero), however, all three bitumen models produced good correlations.

Figure 13:
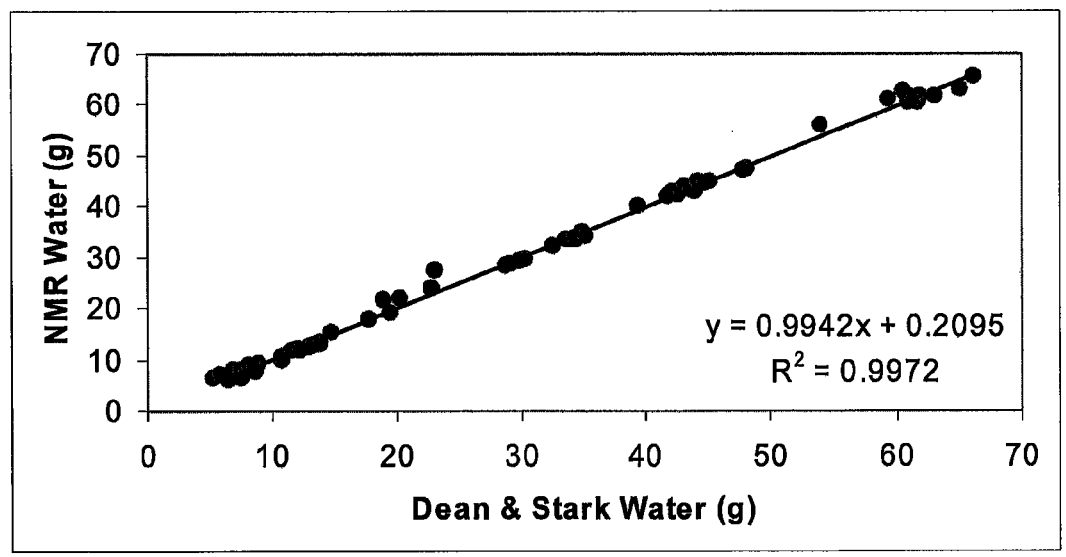
FIG. 13 shows a water chemometric model for extraction samples at room temperature using Pulse Sequence A with the LF90II NMR.
Figure 14:
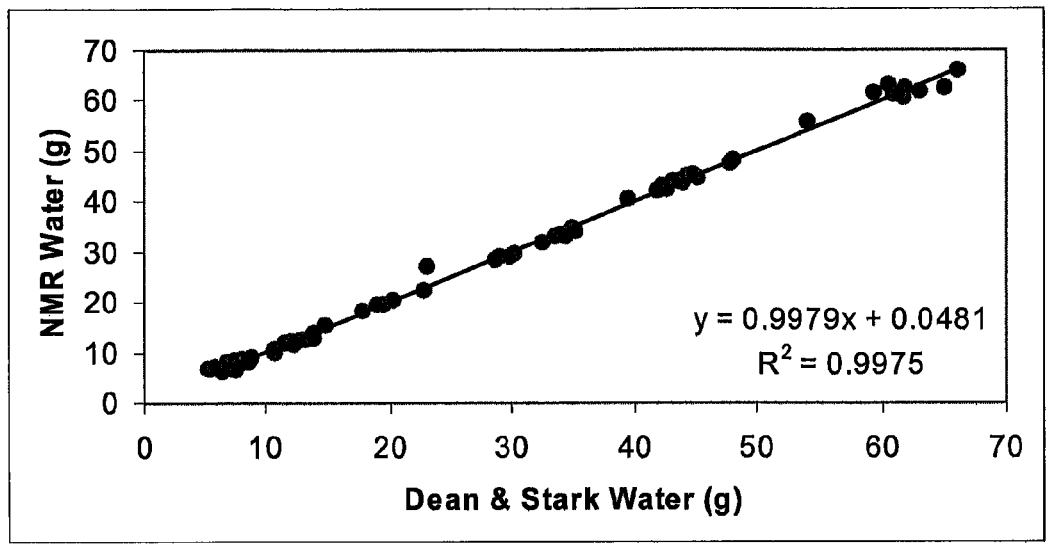
FIG. 14 shows a water chemometric model for extraction samples at 37° C. using Pulse Sequence A with the LF90II NMR.
Figure 15:
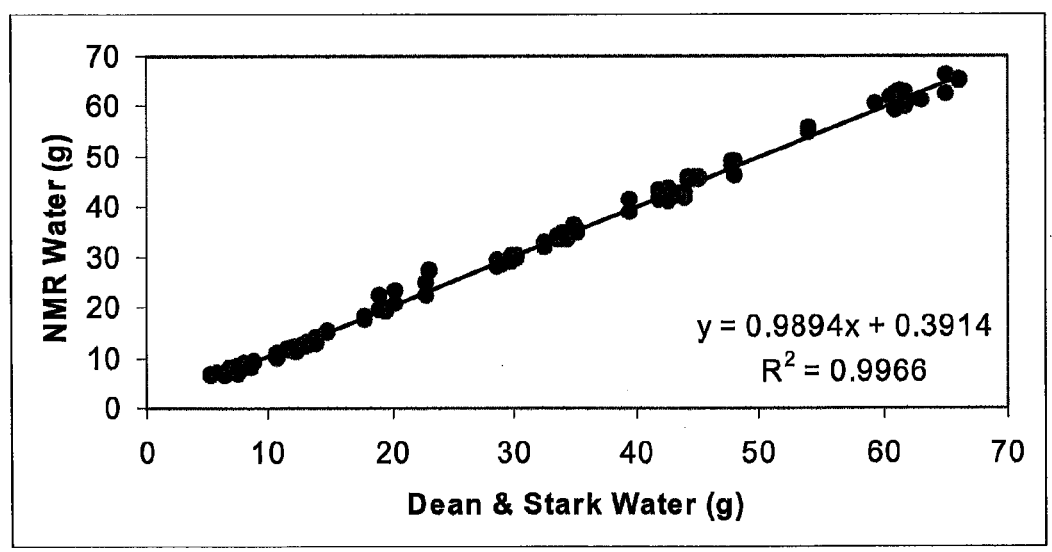
FIG. 15 shows a combined water chemometric model using data collected at room temperature and 37° C. for extraction samples using Pulse Sequence A with the LF90II NMR.

FIG. 13 shows the model for water using the same 64 samples at room temperature. FIG. 14 shows the model for water using the same 64 samples at 37° C. FIG. 15 shows the model for water using the same 64 samples at room temperature and 37° C. Again, the best correlation is obtained at 37° C. All three models again produced good correlations.

Although the best bitumen and water models were obtained at 37° C., a combined room temperature and 37° C. model for bitumen and a separate one for water were used to analyze the following validation samples to demonstrate the level of accuracy and precision that can be obtained using a model with inherent robustness to small temperature variations.

Figure 16:
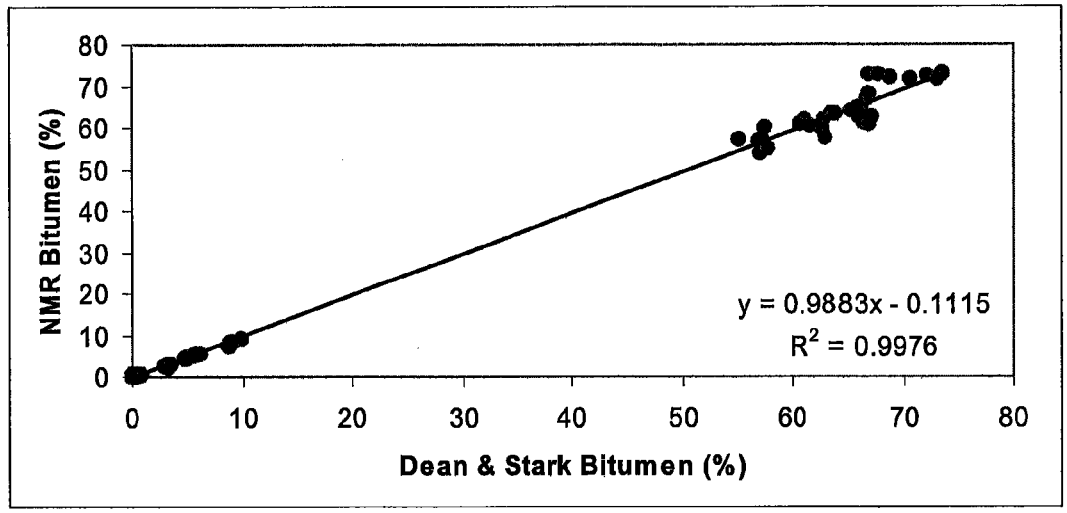
FIG. 16 shows bitumen validation results for extraction samples using combined room temperature and 37° C. model using Pulse Sequence A with the LF90II NMR.
Figure 17:
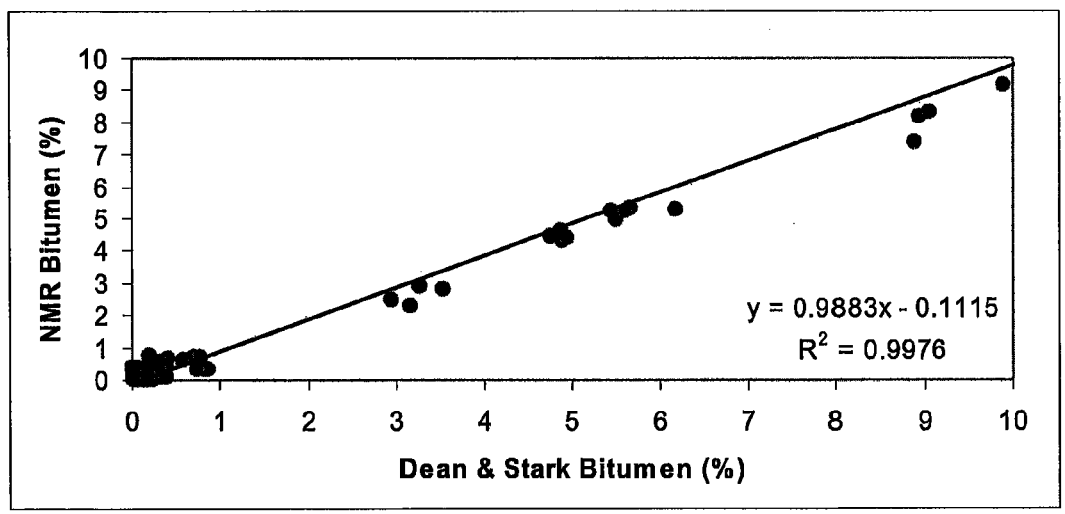
FIG. 17 shows bitumen validation results for extraction samples using combined room temperature and 37° C. model using Pulse Sequence A with the LF90II NMR (zoomed in on low bitumen content samples).
Figure 18:
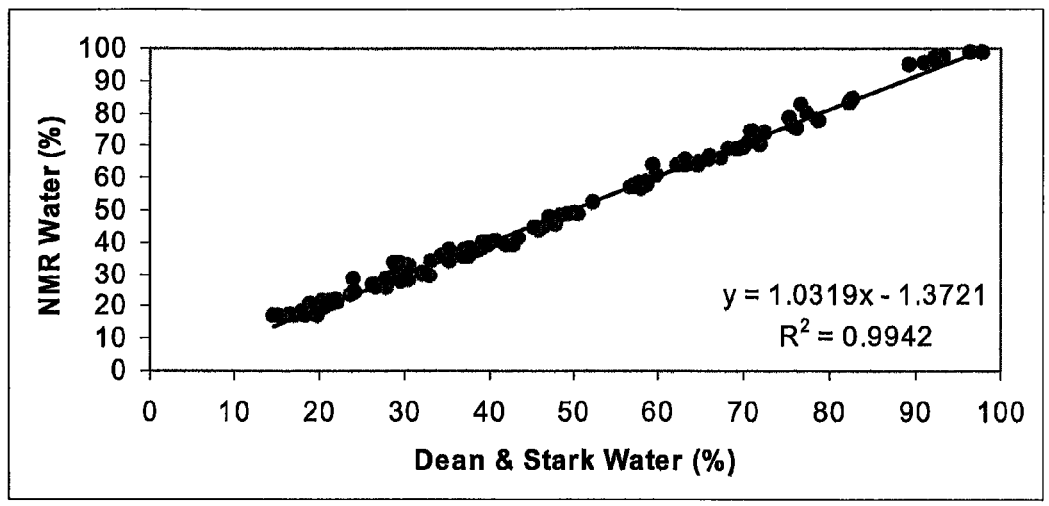
FIG. 18 shows water validation results using combined room temperature and 37° C. model for extraction samples using Pulse Sequence A with the LF90II NMR.

FIGS. 16 and 17 show the bitumen validation data for a variety of process stream samples that were heated to 37° C. and analyzed using a combined room temperature and 37° C. model trained with over 330 extraction samples. A separate low bitumen model, trained with over 230 low bitumen samples (<2.5% bitumen), was used to analyze the low bitumen (<2.5%) validation samples shown in FIGS. 16 and 17. From FIGS. 16 and 17, one can see very good correlations between the present NMR method and Dean-Stark analyses for bitumen and water, respectively. FIG. 18 shows the water validation data for a variety of process stream samples that were heated to 37° C. and analyzed using a combined room temperature and 37° C. model trained with over 330 extraction samples. These results show excellent bitumen and water agreement across a wide range of bitumen and water concentrations for a variety of extraction samples.

Table 2 shows that very good accuracy versus Dean-Stark is achieved. Prior art methods were based on a CPMG pulse sequence which sequence has previously been used for determining oil and water content in oil wells. The CPMG pulse sequence takes advantage of $T_2$ relaxation information only. The use of this pulse sequence is not ideal, as the presence of water associated with clays causes overlap of some of the water signal with the bitumen signal. Kantzas has developed a deconvolution method to correct for this, although this method has not been proven to work well for samples where the bitumen content is very low (<5%) [see Kantzas, A., "Advances in Magnetic Resonance Relaxometry for Heavy Oil and Bitumen Characterization", Journal of Canadian Petroleum Technology, 48 (3) 2009, 15-23]. For these sample-types, a relatively low bitumen signal compared to the water associated with clays signal is expected to cause problems for the deconvolution process. Further, this NMR analysis method takes about 15 minutes per sample to determine both water and bitumen, following sample heating.

For bitumen froth samples (predominantly >50% bitumen), Kantzas reports that average bitumen error compared to Dean & Stark analysis was 3.0% absolute, with a standard deviation of 2.0%, and a maximum error of 10.1% [see Kantzas, A., "Advances in Magnetic Resonance Relaxometry for Heavy Oil and Bitumen Characterization", Journal of Canadian Petroleum Technology, 48 (3) 2009, 15-23]. Their average water error for bitumen froth samples compared to Dean & Stark analysis was 1.9% absolute, with a standard deviation of 1.3%, and a maximum error of 4.6% [see Kantzas, A., "Advances in Magnetic Resonance Relaxometry for Heavy Oil and Bitumen Characterization", Journal of Canadian Petroleum Technology, 48 (3) 2009, 15-23]. The results in Table 2 represent a significant improvement over previous work by others to simultaneously quantify water and bitumen in extraction samples by NMR in terms of accuracy and NMR analysis time.

TABLE 2

NMR accuracy versus Dean-Stark analysis for extraction samples.

| Extraction Samples | Average Difference NMR − DS (% Absolute) | Std Dev of Difference (% Absolute) | Maximum Absolute Difference (% Absolute) |
|---|---|---|---|
| Bitumen (all) | −0.32 | 1.4 | 6.3 |
| Bitumen (>50%) | −0.98 | 2.7 | 6.3 |
| Bitumen (2.5-10%) | −0.61 | 0.31 | 1.5 |
| Bitumen (<2.5%) | −0.04 | 0.17 | 0.56 |
| Water (all) | 0.09 | 1.8 | 5.9 |
| Water (bitumen >50%) | −0.25 | 1.2 | 2.8 |
| Water (bitumen 2.5-10%) | 2.1 | 2.2 | 5.4 |
| Water (bitumen <2.5%) | −0.17 | 1.8 | 5.9 |

Table 3 shows the repeatability of the NMR analysis for a variety of extraction process stream samples. The repeatability data was the result of running the same sample 10 times over the course of one week.

TABLE 3

NMR instrument precision for extraction samples over one week (10 replicates on each sample).

| Extraction Samples | Average Oil (% Absolute) | Oil Std Dev (% Absolute) | Average Water (% Absolute) | Water Std Dev (% Absolute) |
|---|---|---|---|---|
| 24B2 | 72.5 | 0.90 | 17.5 | 0.43 |
| 24B5 | 69.4 | 1.3 | 17.3 | 0.47 |
| 24A5 | 65.6 | 0.61 | 18.6 | 0.57 |
| 24A2 | 62.5 | 0.68 | 21.7 | 0.66 |
| 24B8 | 60.2 | 0.42 | 26.6 | 0.33 |
| 24A8 | 56.7 | 0.55 | 27.2 | 0.52 |
| 23B1 | 8.08 | 0.38 | 28.5 | 0.25 |
| 24A9 | 4.81 | 0.31 | 28.1 | 0.35 |
| 24B9 | 4.47 | 0.41 | 27.8 | 0.14 |
| 24B4 | 2.81 | 0.23 | 94.1 | 1.4 |
| 24A4 | 1.75 | 0.15 | 98.1 | 0.89 |
| 24A3 | 0.44 | 0.05 | 51.4 | 0.29 |
| 24B7 | 0.40 | 0.12 | 34.4 | 0.19 |
| 24B3 | 0.18 | 0.04 | 70.0 | 0.55 |
| 24A7 | 0.15 | 0.05 | 35.1 | 0.19 |

Repeatability for bitumen froth samples ranged from 0.42% to 1.3% absolute (1 standard deviation). For samples with intermediate bitumen content (2.5-10%), repeatability ranged from 0.23% to 0.41% absolute (1 standard deviation). For low bitumen samples (<2.5%), repeatability ranged from 0.05% to 0.15% absolute (1 standard deviation). For all extraction samples, the water repeatability ranged from 0.14% to 1.4% absolute (1 standard deviation).

EXAMPLE 2

Eighty five oil sand samples from three separate mine core holes in the Athabasca oil sand deposit in Alberta, were sub-sampled in separate containers and analyzed by Dean-Stark extraction and by using a Bruker mq10 low field NMR instrument ($^1$H frequency 10 MHz, Magnetic Field 0.23 T). The NMR samples were sampled into Teflon vials purchased from VWR International (PTFE jars, 15 ml, 34 mm height, 34 mm cap diameter, part number: 89026-160). This provides a container that fits inside the smaller mq10 instrument while keeping the entire sample within the sensitive region of the NMR probe. The Dean-Stark results were used as the accepted values for training sets and validation results.

In addition, 58 core hole samples from two separate core holes were sub-sampled into 250 ml Nalgene containers for analysis using the larger LF90II low field NMR instrument as described above.

Two pulse sequences were tested on oil sand samples using the mq10 instrument and the LF90II instrument described above. The pulse sequence that was optimized for oil sand extraction process streams (Pulse Sequence A) was compared with a modified pulse sequence, optimized for oil sand samples (Pulse Sequence B). On the mq10 instrument, better oil sand correlations were obtained using an NMR probe with a dead time of 0.0277 milliseconds compared to 0.0097 milliseconds.

The optimized Pulse Sequence B for oil sand samples used 50 transverse relaxation echoes acquired at 27 $T_1$ points, exponentially spread from 1 ms through 200 ms. The final stretch of $T_2$ measurement comprised of 1000 echoes spaced 0.15 ms apart. Thirty two replicate scans of this pulse sequence produce adequate signal to noise ratios to measure oil sand samples with acceptable accuracy and precision, yielding an NMR analysis time of about 90 seconds.

Oil sand sample weights varied from 10 g to 30 g for the mq10 samples in Teflon vials. These samples were preheated to 40° C. in an oven prior to analysis in the mq10. This keeps the samples the same temperature as the mq10 NMR probe. For the LF90II, oil sand sample weights varied from 40 g to 200 g in Nalgene bottles. These samples were preheated to 37° C. prior to analysis to maintain the same temperature as the LF90II NMR probe.

After the raw TD-NMR data was collected for each sample, the raw data files were loaded into the OPUS software along with the corresponding Dean-Stark reference bitumen and water values. The OPUS software was used to build chemometric models using partial least square technique to determine bitumen and water content from the raw TD-NMR signal. Two thirds of the samples were designated as a training set while the other third were designated as validation samples.

Figure 19:
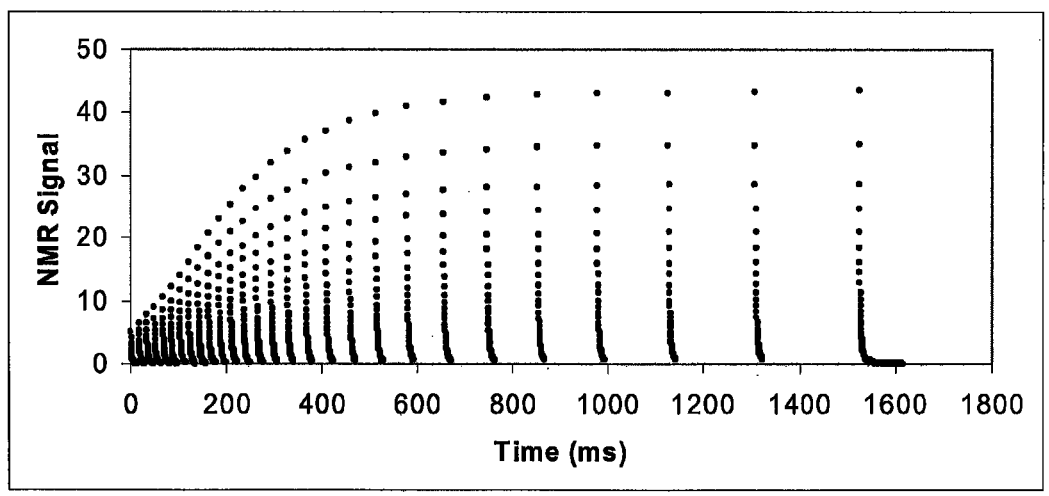
FIG. 19 shows the NMR signal versus time for a typical oil sand sample on mq10 NMR using Pulse Sequence B (average of 32 scans, 90 seconds analysis time).
Figure 20:
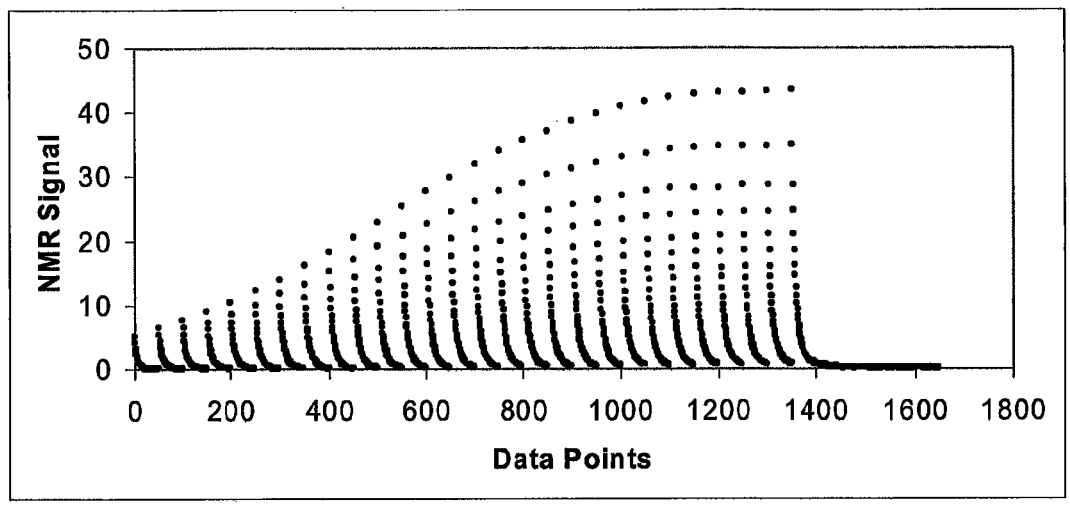
FIG. 20 shows the NMR signal versus data points for a typical oil sand sample on mq10 NMR using Pulse Sequence B (average of 32 scans, 90 seconds analysis time).
Figure 21:
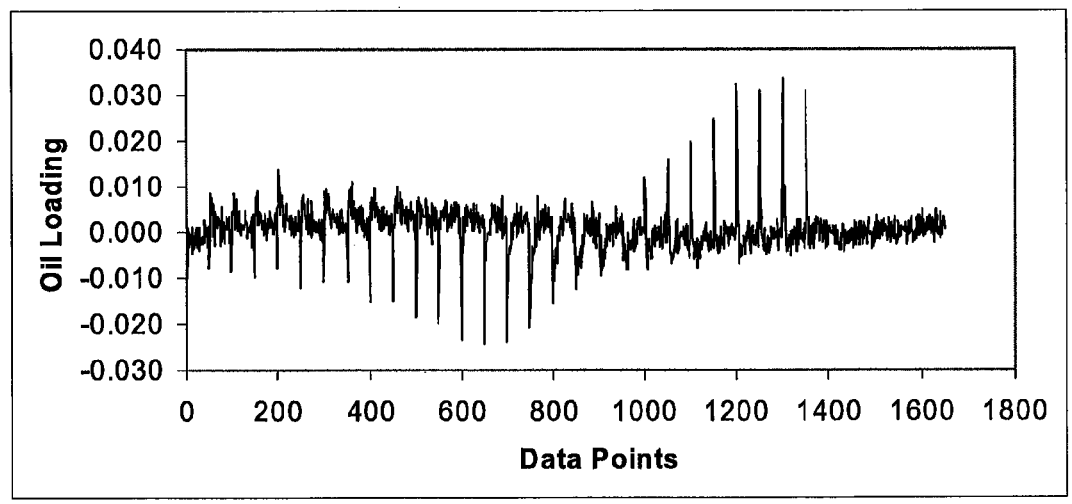
FIG. 21 shows the partial least squares bitumen model loadings for oil sand samples on mq10 NMR using Pulse Sequence B (32 scans, 90 seconds analysis time).
Figure 22:
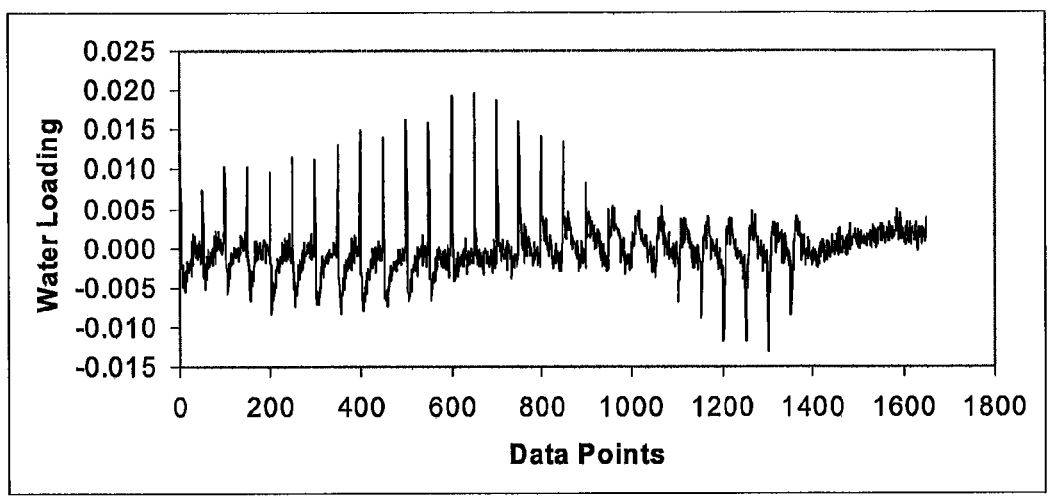
FIG. 22 shows the partial least squares water model loadings for oil sand samples on mq10 NMR using Pulse Sequence B (32 scans, 90 seconds analysis time).

FIG. 19 shows the raw data (NMR signal versus time) for a typical oil sand sample on mq10 NMR using Pulse Sequence B (average of 32 scans, 90 seconds analysis time). FIG. 20 shows the raw data (NMR signal versus data points) for a typical oil sand sample on mq10 NMR using Pulse Sequence B (average of 32 scans, 90 seconds analysis time). FIG. 21 shows the partial least squares bitumen model loadings for oil sand samples on mq10 NMR using Pulse Sequence B (32 scans, 90 seconds analysis time) and FIG. 22 shows the partial least squares water model loadings for oil sand samples on mq10 NMR using Pulse Sequence B (32 scans, 90 seconds analysis time).

Figure 23:
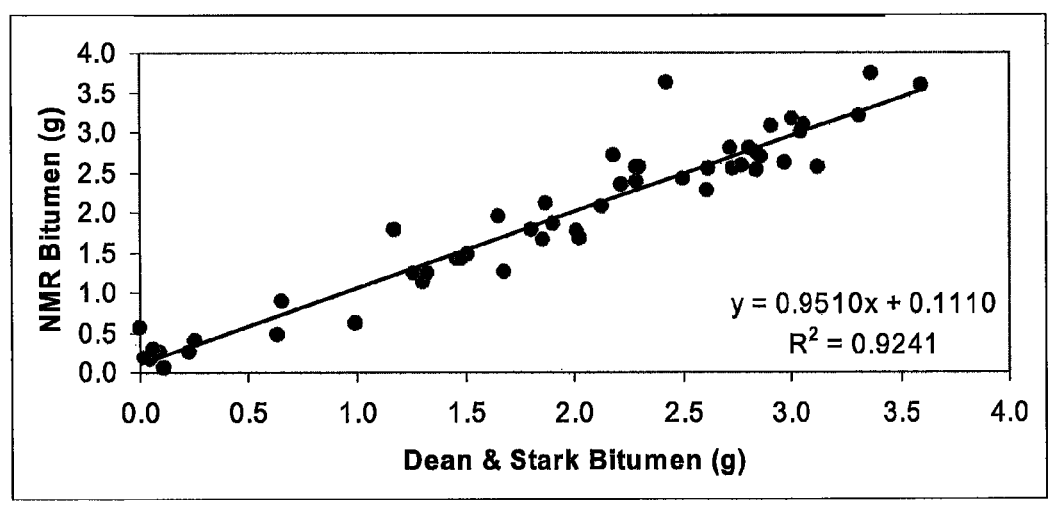
FIG. 23 shows a chemometric model for bitumen in oil sand samples developed with data from a mq10 NMR using Pulse Sequence A (4 scans, 90 seconds analysis time).
Figure 24:
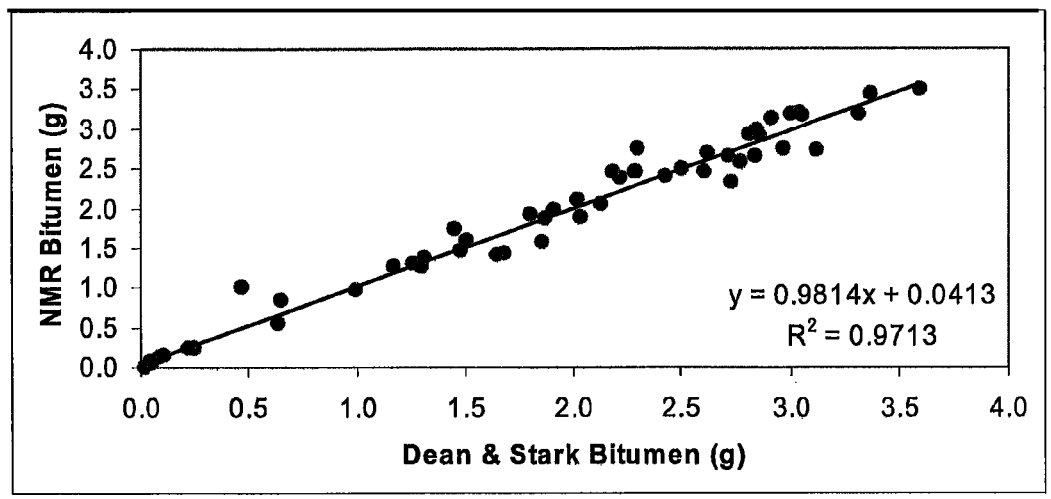
FIG. 24 shows a chemometric model for bitumen in oil sand samples developed with data from a mq10 NMR using Pulse Sequence B (32 scans, 90 seconds analysis time).

FIG. 23 and FIG. 24 show the bitumen models using 54 oil sand samples on the mq10 low field NMR instrument. FIG. 23 shows the bitumen model using Pulse Sequence A previously used for extraction samples (4 scans). FIG. 24 shows the bitumen model using Pulse Sequence B that was optimized for oil sand samples (32 scans).

Figure 25:
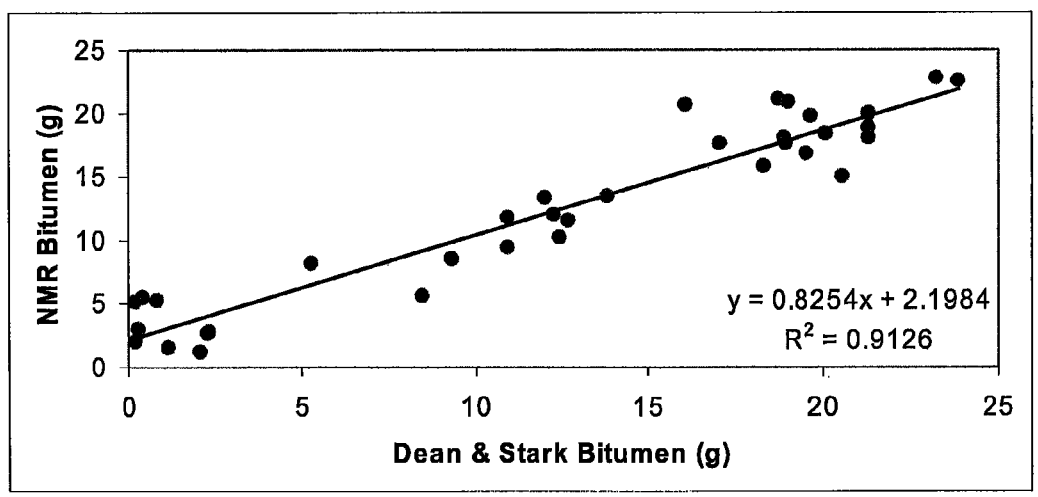
FIG. 25 shows a chemometric model for bitumen in oil sand samples developed with data from a LF90II NMR using Pulse Sequence A (4 scans, 90 seconds analysis time).
Figure 26:
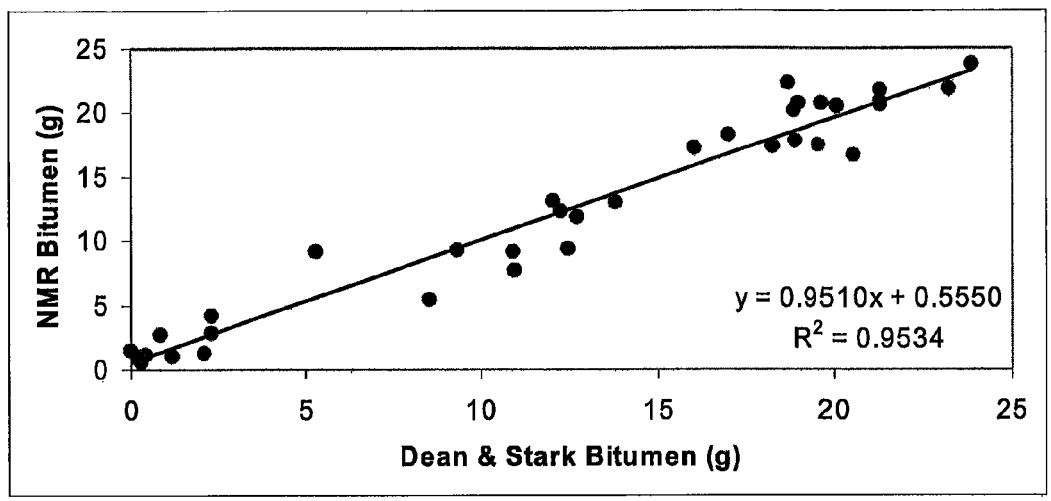
FIG. 26 shows a chemometric model for bitumen in oil sand samples developed with data from a LF90II NMR using Pulse Sequence B (4 scans, <20 seconds analysis time).

FIG. 25 and FIG. 26 show the models for bitumen using 37 oil sand samples on the LF90II low field NMR instrument. FIG. 25 shows the bitumen model using Pulse Sequence A (4 scans) and FIG. 26 shows the bitumen model using Pulse Sequence B (4 scans).

The best bitumen model (R-squared closest to 1, slope closest to 1, and y-intercept closest to zero) is the model on the mq10 using Pulse Sequence B with 32 scans. Without being bound to theory, it is believed that Pulse Sequence B, with its shortened timings, gathers more information at shorter relaxation times, where bitumen and water associated with clays tend to produce overlapping signals [Bryan, J., Mai, A., Hum, F. M., Kantzas, A., "Oil and Water Content Measurements in Bitumen Ore and Froth Samples using Low-Field NMR", SPE Reservoir Evaluation & Engineering, 9 (6) 2006, 654-663]. Given the much higher solids to water ratio of oil sand samples compared to extraction process stream samples, a much higher percentage of the water in oil sand is associated with clay solids, resulting in more overlap between the bitumen and water signals. As a result, more data is required at shorter relaxation times using Pulse Sequence B to achieve good results with oil sand samples. The shorter total duration of the pulse sequence also allows more scans to be performed in the same analysis time (90 seconds), resulting in a higher signal to noise ratio.

Figure 27:
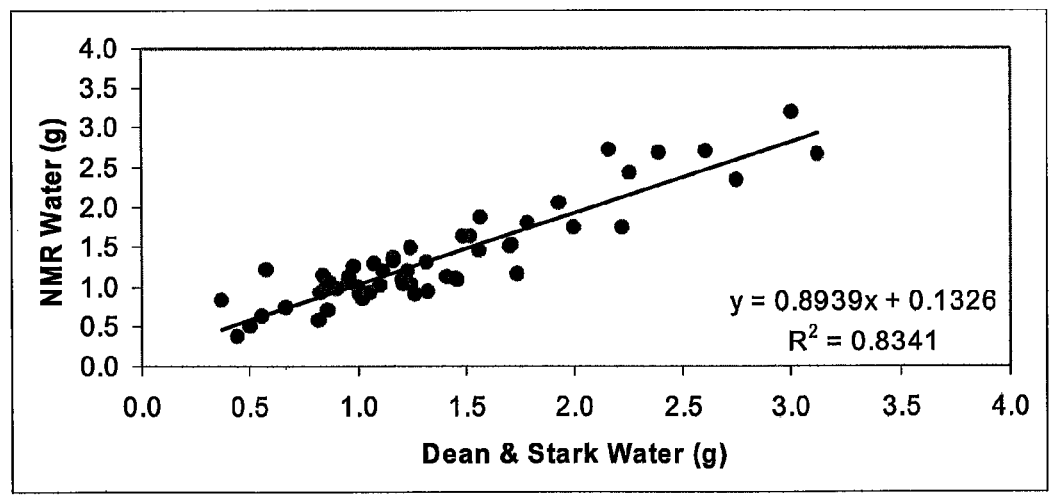
FIG. 27 shows a chemometric model for water in oil sand samples developed with data from a mq10 NMR using Pulse Sequence A (4 scans, 90 seconds analysis time).
Figure 28:
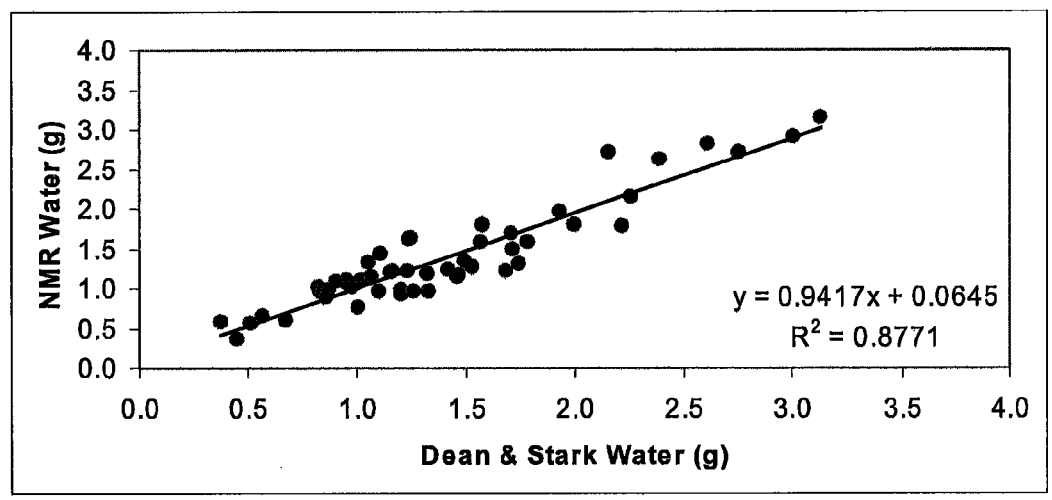
FIG. 28 shows a chemometric model for water in oil sand samples developed with data from a mq10 NMR using Pulse Sequence B (32 scans, 90 seconds analysis time).

FIGS. 27 to 28 show the models for water using 54 oil sand samples on the mq10 low field NMR instrument. FIG. 27 shows the water model using Pulse Sequence A and FIG. 28 shows the water model using Pulse Sequence B.

Figure 29:
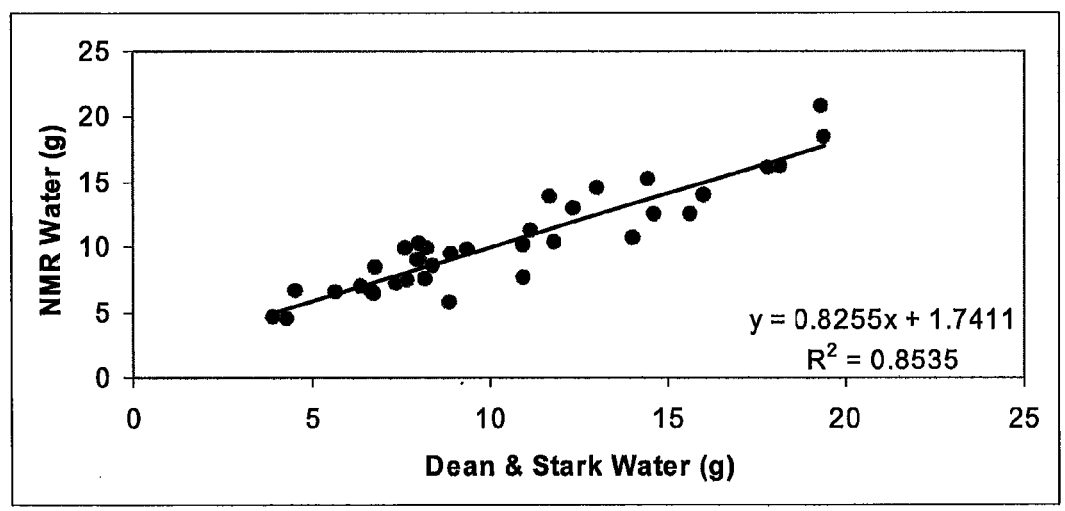
FIG. 29 shows a chemometric model for water in oil sand samples developed with data from a LF90II NMR using Pulse Sequence A (4 scans, 90 seconds analysis time) for oil sand samples.
Figure 30:
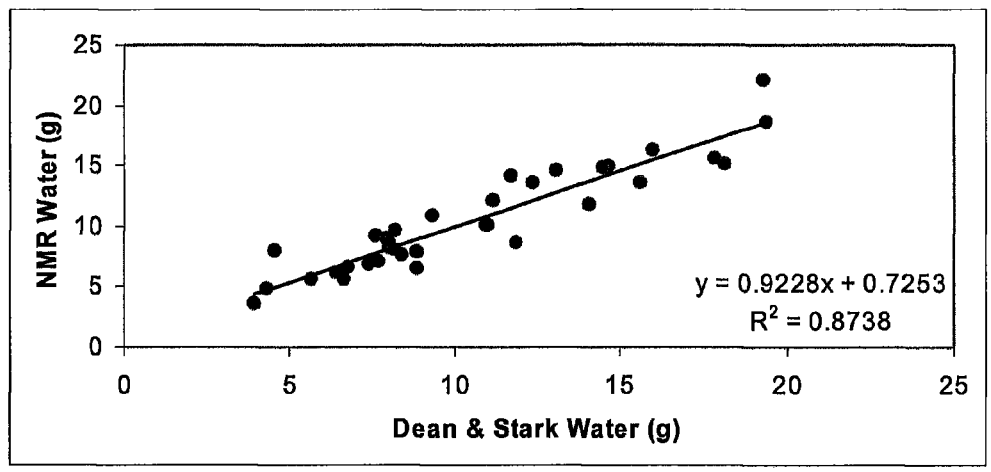
FIG. 30 shows a chemometric model for water in oil sand samples developed with data from a LF90II NMR using Pulse Sequence B (4 scans, <20 seconds analysis time).
Figure 31:
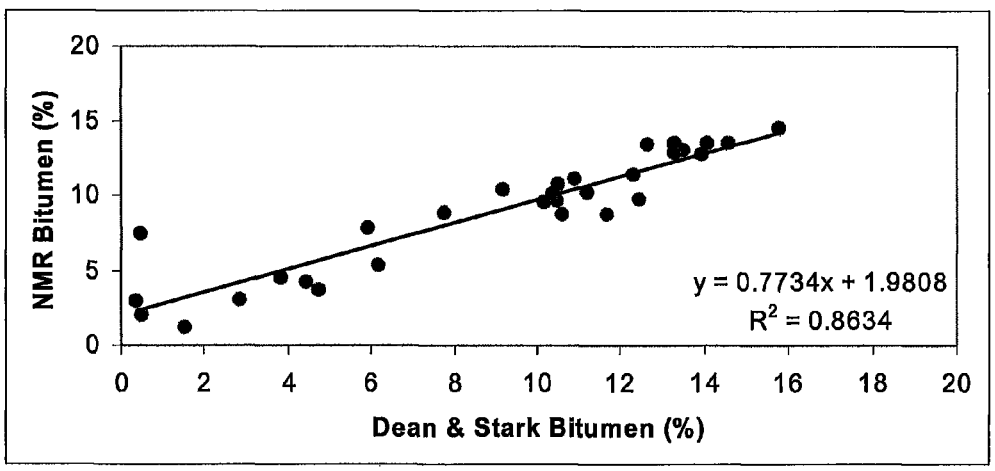
FIG. 31 shows bitumen validation data on mq10 NMR for oil sand samples using Pulse Sequence A (4 scans, 90 seconds analysis time, 30 samples).

FIGS. 29 and 30 show the models for water using 37 oil sand samples on the LF90II low field NMR instrument. FIG. 29 shows the water model using Pulse Sequence A and FIG. 30 shows the water model using Pulse Sequence B. The best water model is the model on the mq10 NMR using Pulse Sequence B and 32 scans for likely the same reasons as discussed above.

Figure 32:
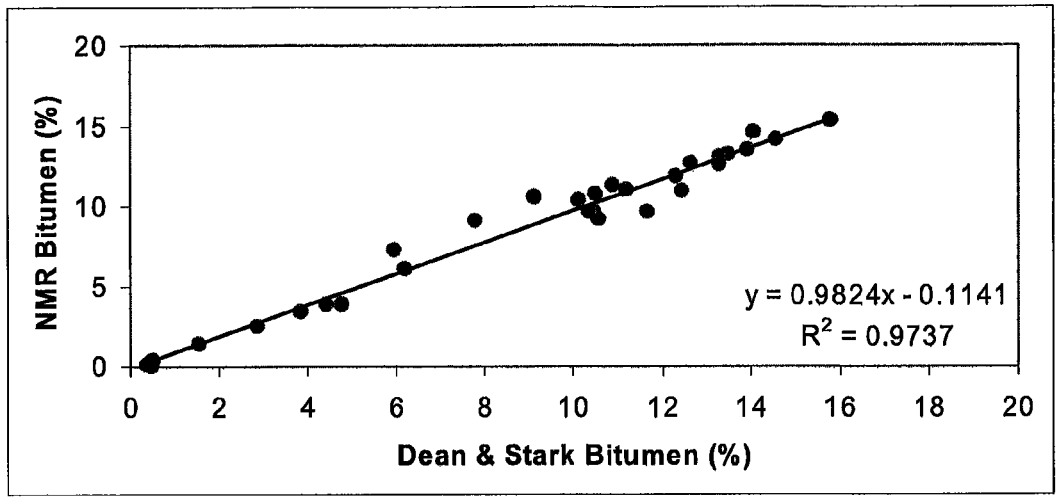
FIG. 32 shows bitumen validation data on mq10 NMR for oil sand samples using Pulse Sequence B (32 scans, 90 seconds analysis time, 30 samples).
Figure 33:
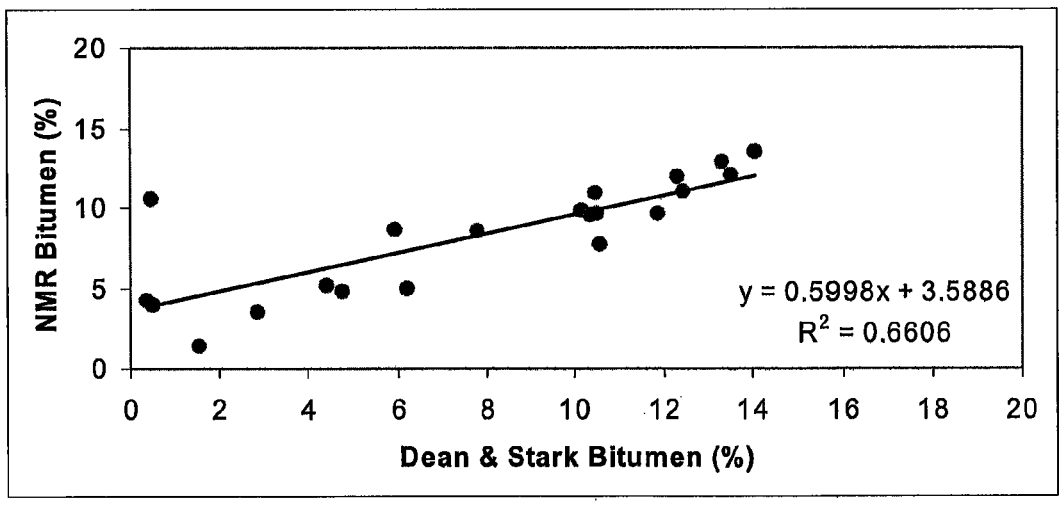
FIG. 33 shows bitumen validation data on LF90II NMR for oil sand samples using Pulse Sequence A (4 scans, 90 seconds analysis time, 21 samples).
Figure 34:
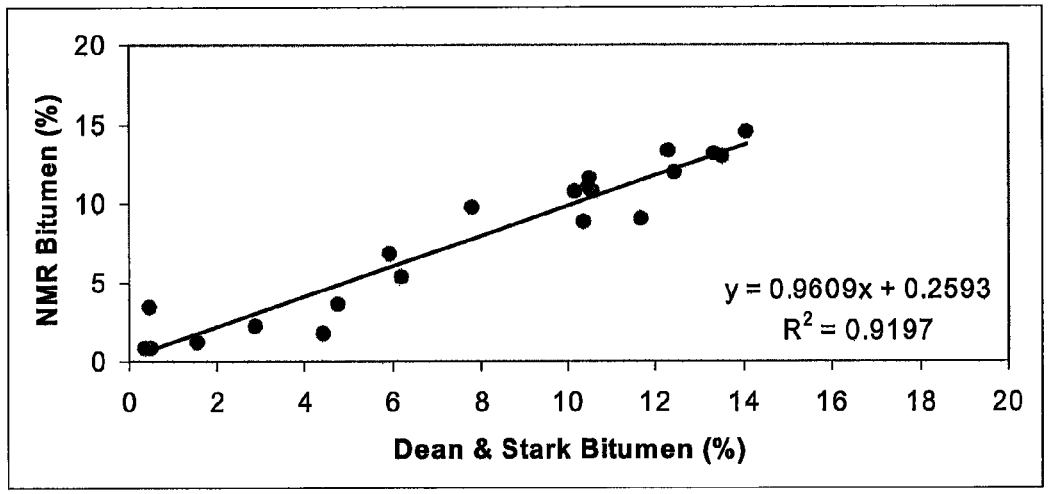
FIG. 34 shows bitumen validation data on LF90II NMR for oil sand samples using Pulse Sequence B (4 scans, <20 seconds analysis time, 21 samples).
Figure 35:
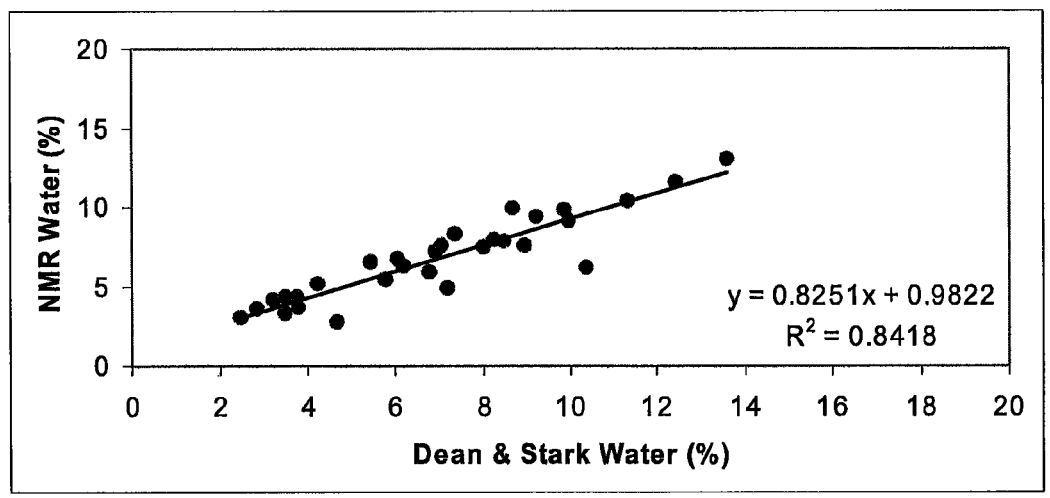
FIG. 35 shows water validation data on mq10 NMR for oil sand samples using Pulse Sequence A (4 scans, 90 seconds analysis time, 30 samples).
Figure 36:
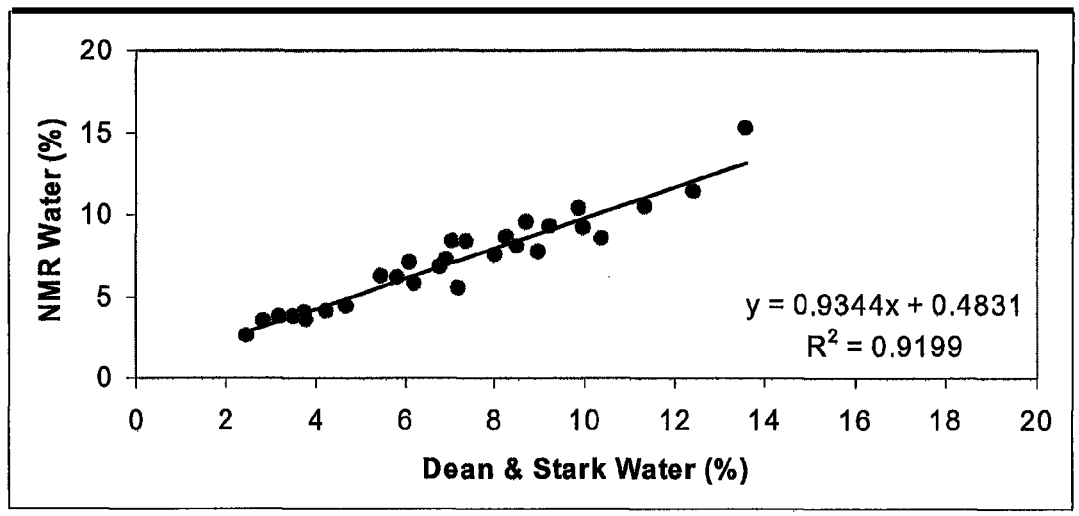
FIG. 36 shows water validation data on mq10 NMR for oil sand samples using Pulse Sequence B (32 scans, 90 seconds analysis time, 30 samples).
Figure 37:
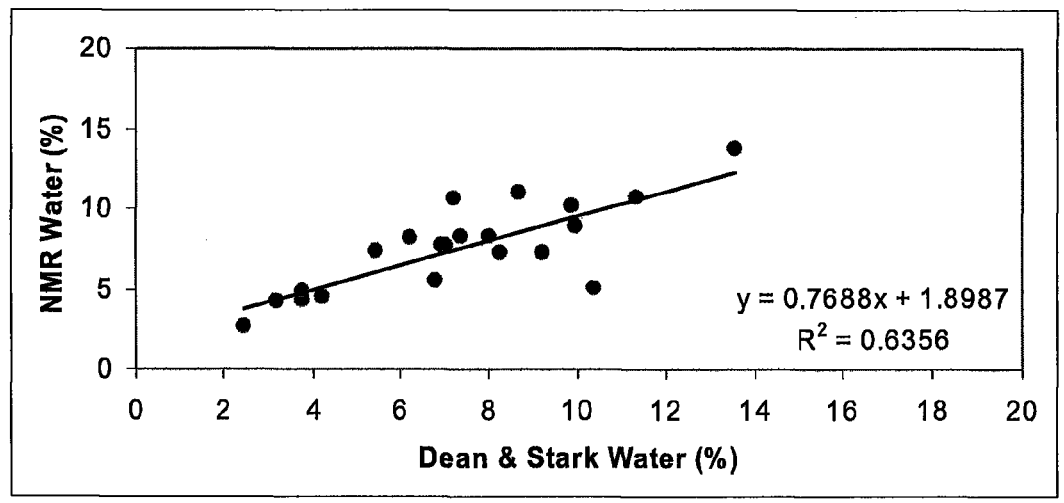
FIG. 37 shows water validation data on LF90II NMR for oil sand samples using Pulse Sequence A (4 scans, 90 seconds analysis time, 21 samples).
Figure 38:
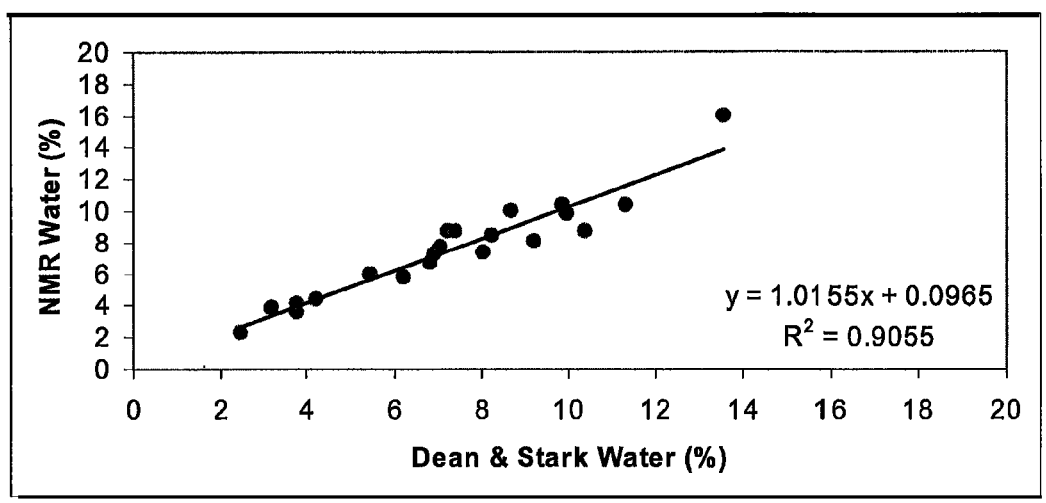
FIG. 38 shows water validation data on LF90II NMR for oil sand samples using Pulse Sequence B (4 scans, <20 seconds analysis time, 21 samples).

FIGS. 31 to 34 show the bitumen validation data for the various bitumen models shown above. In each case, about ⅓ of the samples were used as a validation test set. The best overall correlation for the bitumen validation results was obtained on the mq10 NMR using Pulse Sequence B and 32 scans (FIG. 32).

FIGS. 35 to 38 show the water validation data for the various water models shown above. The water validation results obtained on the mq10 NMR using Pulse Sequence B and 32 scans (FIG. 36) and the water validation results obtained on the LF90II using Pulse Sequence B with 4 scans (FIG. 37) both produced very good correlations.

Table 4 compares the accuracy of the validation results obtained under different conditions. All conditions produced low average biases <0.5% absolute for both bitumen and water. The validation results obtained on the mq10 using Pulse Sequence B and 32 scans produced the lowest standard deviation of the differences and lowest maximum absolute difference for both bitumen and water. The maximum absolute error for bitumen and water under these conditions is quite small at only 2.0% and 1.8% absolute respectively. Thus, excellent agreement between the fast bitumen and water NMR method is achieved versus Dean-Stark analysis for oil sand samples.

TABLE 4

NMR accuracy versus Dean-Stark analysis for oil sand samples.

| Conditions | Average Difference NMR − DS (% Absolute) | Std Dev of Difference (% Absolute) | Maximum Absolute Difference (% Absolute) |
|---|---|---|---|
| Bitumen Validation | — | — | — |
| Mq10, PS A, LD, 4 scans | −0.06 | 1.8 | 7.0 |
| Mq10, PS B, LD, 32 scans | −0.27 | 0.77 | 2.0 |
| LF90II, PS A, 4 scans | 0.45 | 2.8 | 10.1 |
| LF90II, PS B, 4 scans | −0.02 | 1.4 | 2.9 |
| Water Validation | — | — | — |
| Mq10, PS A, 4 scans | −0.25 | 1.2 | 4.2 |
| Mq10, PS B, 32 scans | 0.01 | 0.84 | 1.8 |
| LF90II, PS A, 4 scans | 0.20 | 1.8 | 5.4 |
| LF90II, PS B, 4 scans | 0.19 | 0.94 | 2.4 |

Note:
PS = Pulse sequence

As a comparison to the prior art, Kantzas reported the average bitumen error for oil sand samples compared to Dean-Stark analysis as 1.0% absolute, with a standard deviation of 0.95%, and a maximum error of 6.5% [Kantzas, A., "Advances in Magnetic Resonance Relaxometry for Heavy Oil and Bitumen Characterization", Journal of Canadian Petroleum Technology, 48 (3) 2009, 15-23.]. The average water error for oil sand samples compared to Dean-Stark analysis was 0.92% absolute, with a standard deviation of 0.74%, and a maximum error of 4.2% [Kantzas, A., "Advances in Magnetic Resonance Relaxometry for Heavy Oil and Bitumen Characterization", Journal of Canadian Petroleum Technology, 48 (3) 2009, 15-23.]. The best results in Table 4 represent a significant improvement over previous work by others to simultaneously quantify water and bitumen in oil sand samples by NMR in terms of accuracy and NMR analysis time.

Table 5 shows the repeatability for a variety of oil sand samples under the best conditions using the mq10 NMR instrument with Pulse Sequence B and 32 scans. The repeatability data was collected in a single day on the same sample. Excellent repeatability is obtained with 32 scans, with average 1 standard deviation errors of only 0.06% absolute for both bitumen and water. The average 1 standard deviation errors for bitumen and water were reduced 2-3 fold by increasing the scans from 4 to 32.

TABLE 5

NMR instrument same day repeatability for oil sand samples (10 replicates on each sample).

| Oil Sand Sample | Average Oil (% Absolute) | Oil Std Dev (% Absolute) | Average Water (% Absolute) | Water Std Dev (% Absolute) |
|---|---|---|---|---|
| Sample A | 16.31 | 0.03 | 3.02 | 0.08 |
| Sample B | 0.28 | 0.09 | 9.54 | 0.08 |
| Sample C | 3.44 | 0.07 | 12.67 | 0.05 |
| Sample D | 9.06 | 0.06 | 7.38 | 0.03 |
| Average: | — | 0.06 | — | 0.06 |

Conditions: Mq10 NMR, Pulse Sequence B, 32 scans.

Figure 39:
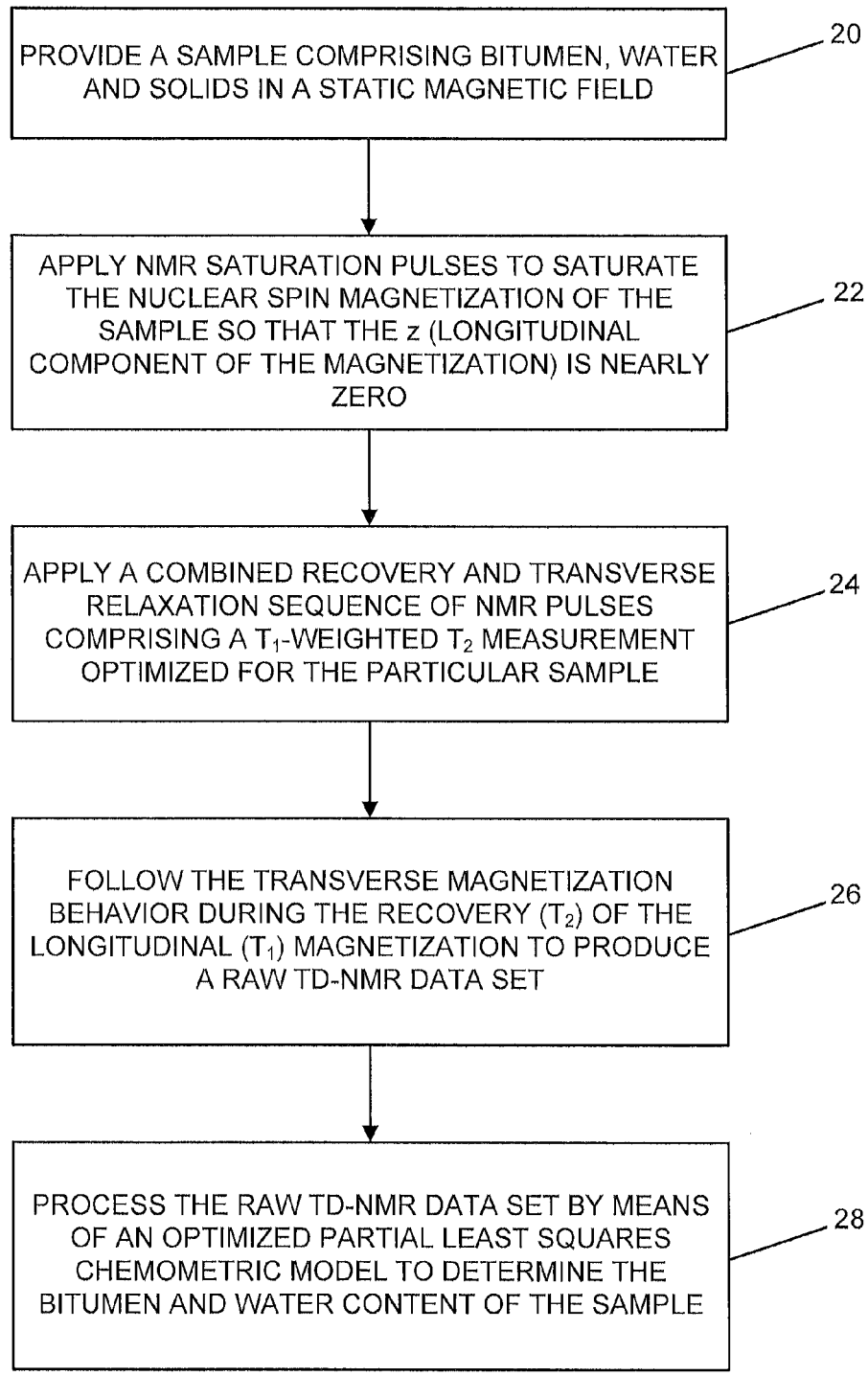
FIG. 39 is a flow chart of a method of the invention.

FIG. 39 shows a nuclear magnetic resonance (NMR) method for determining bitumen and water content in an oil sand sample or an oil sand extraction sample. At 20, a sample comprising bitumen, water and solids is provided in a static magnetic field which aligns the nuclear spin systems in the sample so that a net magnetization vector is produced aligned with the external magnetic field direction, called the "longitudinal" or "Z-axis" direction in common NMR terminology. At 22, NMR saturation pulses are then applied to the sample to saturate the nuclear spin magnetization so that the z (longitudinal) component of the magnetization is nearly zero. At 24, a combined recovery and transverse relaxation sequence of NMR pulses comprising a $T_1$-weighted $T_2$ measurement optimized for the particular sample is then applied to the sample. At 26, the transverse ($T_2$) magnetization behavior is followed during the recovery period of the longitudinal ($T_1$) magnetization to produce a raw TD-NMR data set. At 28, the raw TD-NMR data set is processed by means of an optimized partial least squares chemometric model to determine the bitumen and water content of the sample.

The previous description of the disclosed embodiments is provided to enable any person skilled in the art to make or use the present invention. Various modifications to those embodiments will be readily apparent to those skilled in the art, and the generic principles defined herein may be applied to other embodiments without departing from the spirit or scope of the invention. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims.

We claim:

1. A method for quantifying bitumen and/or water in a sample comprising bitumen, water and solids using a time-domain nuclear magnetic resonance pulse spectrometer, comprising the steps of:
   (a) initially saturating the magnetization of the sample so that essentially no magnetization remains in the +Z axis;
   (b) subjecting the sample to a sequence of radio-frequency pulses optimized for the measurement of bitumen and water in the sample;
   (c) allowing the recording of the transverse relaxation ($T_2$) echo trains after incremental longitudinal relaxation to produce a raw TD-NMR data set for the sample; and
   (d) providing a computer which has been programmed to determine and display the amount of bitumen and water in the sample by means of an optimized partial least squares chemometric model relating raw TD-NMR data sets obtained from a training set of samples comprising bitumen, water and solids to the training samples' corresponding reference values obtained from an analysis method for determining the quantity of bitumen and water.

2. The method of claim 1, wherein the magnetization of the sample is saturated by applying 10 rapid 90° radio-frequency (RF) pulses to the sample.

3. The method of claim 1, wherein the sample is an oil sand extraction process sample and the optimized sequence of radio-frequency pulses is such that there are 50 transverse relaxation echoes acquired at 27 $T_1$ points, exponentially spread from 20 ms through 3000 ms, and the final stretch of $T_2$ measurement comprises 1000 echoes spaced 0.25 ms apart.

4. The method of claim 1, wherein the sample is an oil sand sample and the optimized sequence of radio-frequency pulses is such that there are 50 transverse relaxation echoes acquired at 27 $T_1$ points, exponentially spread from 1 ms through 200 ms, and the final stretch of $T_2$ measurement comprises 1000 echoes spaced 0.15 ms apart.

5. The method of claim 1, wherein the standard analysis method is Dean-Stark extraction for measuring water and bitumen in the reference sample.

6. The method of claim 1, wherein the sample is heated to 37° C. or 40° C. prior to quantification to match the temperature of the NMR probe.

7. The method of claim 3, wherein the time to obtain the raw TD-NMR data set for the sample is about 90 seconds.

8. The method of claim 4, wherein the time to obtain the raw TD-NMR data set for the sample is about 90 seconds.

* * * * *